(12) United States Patent
Neyer et al.

(10) Patent No.: US 7,597,790 B2
(45) Date of Patent: Oct. 6, 2009

(54) FLOW CONTROL SYSTEMS

(75) Inventors: David W. Neyer, Castro Valley, CA (US); Phillip H. Paul, Livermore, CA (US); Don Wesley Arnold, Livermore, CA (US); Christopher G. Bailey, Pleasanton, CA (US)

(73) Assignee: Eksigent Technologies, LLC, Dublin, CA (US)

( * ) Notice: Subject to any disclaimer, the term of this patent is extended or adjusted under 35 U.S.C. 154(b) by 875 days.

(21) Appl. No.: 10/480,691

(22) PCT Filed: Jun. 13, 2002

(86) PCT No.: PCT/US02/19121

§ 371 (c)(1), (2), (4) Date: Dec. 10, 2003

(87) PCT Pub. No.: WO02/101474

PCT Pub. Date: Dec. 19, 2002

(65) Prior Publication Data

US 2004/0163957 A1    Aug. 26, 2004

(51) Int. Cl.
*B01D 57/02* (2006.01)
(52) U.S. Cl. ............... 204/450; 204/451; 204/454; 204/600; 204/601
(58) Field of Classification Search ............... 204/450, 204/451, 454, 600, 601
See application file for complete search history.

(56) References Cited

U.S. PATENT DOCUMENTS

| | | | |
|---|---|---|---|
| 2,615,940 A | 10/1952 | Williams | 171/330 |
| 2,644,900 A | 7/1953 | Hardway, Jr. | 310/2 |
| 2,644,902 A | 7/1953 | Hardway, Jr. | 310/2 |
| 2,661,430 A | 12/1953 | Hardway, Jr. | 310/2 |
| 2,995,714 A | 8/1961 | Hannah | 331/107 |
| 3,143,691 A | 8/1964 | Hurd | 317/231 |
| 3,209,255 A | 9/1965 | Estes et al. | 324/94 |

(Continued)

FOREIGN PATENT DOCUMENTS

CN    2286429 Y    7/1998

(Continued)

OTHER PUBLICATIONS

International Search Report, for PCT Application No. PCT/US03/30008, mailed Mar. 4, 2004, 4 pages.

(Continued)

*Primary Examiner*—Arun S Phasge
(74) *Attorney, Agent, or Firm*—Michael Fredrick; Kristin Hiibner; Sheldon Mak Rose & Anderson

(57) ABSTRACT

A flow controller which uses a combination of hydrostatic pressure and electroosmotic flow to control the flow of a fluid. A driving fluid (1204) whose flow rate is dependent on both hydrostatic pressures and electroosmotic flow can be used (a) directly as a working fluid in an operable device, for example a chromatograph, or (b) to displace a working fluid (1203) from a storage container (625) into an operable device (1301), or both (a) and (b). The driving fluid (1204) can be composed of one or more fluids. Part or all the driving fluid (1204) is passed through an electroosmotic device (100) so as to increase or decrease the flow rate induced by hydrostatic pressure.

8 Claims, 20 Drawing Sheets

U.S. PATENT DOCUMENTS

| | | | |
|---|---|---|---|
| 3,427,978 A | 2/1969 | Hanneman et al. | 103/1 |
| 3,544,237 A | 12/1970 | Walz | 417/48 |
| 3,682,239 A | 8/1972 | Abu-Romia | 165/1 |
| 3,921,041 A | 11/1975 | Stockman | |
| 3,923,426 A | 12/1975 | Theeuwes | 417/48 |
| 4,347,131 A | 8/1982 | Brownlee | 210/101 |
| 4,638,444 A | 1/1987 | Laragione et al. | 364/510 |
| 4,681,678 A | 7/1987 | Leaseburge et al. | 210/101 |
| 4,684,465 A | 8/1987 | Leaseburge et al. | 210/198.2 |
| 4,767,279 A | 8/1988 | Dourdeville et al. | 417/18 |
| 4,810,392 A | 3/1989 | Fulton et al. | 210/659 |
| 4,921,041 A | 5/1990 | Akachi | 165/104.29 |
| 5,032,264 A | 7/1991 | Geiger | |
| 5,040,126 A | 8/1991 | Allington | 364/510 |
| 5,219,020 A | 6/1993 | Akachi | 165/104.26 |
| 5,249,929 A | 10/1993 | Miller et al. | 417/207 |
| 5,302,264 A | 4/1994 | Welch et al. | |
| 5,312,233 A | 5/1994 | Tanny et al. | 417/316 |
| 5,418,079 A | 5/1995 | Diethelm | 429/26 |
| 5,429,728 A | 7/1995 | Gordon | |
| RE35,010 E | 8/1995 | Price | 222/1 |
| 5,482,608 A | 1/1996 | Keely et al. | |
| 5,573,651 A | 11/1996 | Dasgupta et al. | 204/601 |
| 5,630,706 A | 5/1997 | Yang | 417/3 |
| 5,664,938 A | 9/1997 | Yang | 417/313 |
| 5,670,707 A | 9/1997 | Fennell et al. | 73/1 |
| 5,777,213 A | 7/1998 | Tsukazaki et al. | 73/61.52 |
| 5,797,719 A | 8/1998 | James et al. | 417/46 |
| 5,814,742 A | 9/1998 | Vissers et al. | 73/863.73 |
| 5,858,193 A | 1/1999 | Zanzucchi et al. | 204/601 |
| 5,888,050 A | 3/1999 | Fitzgerald | 417/46 |
| 5,915,401 A | 6/1999 | Menard et al. | 137/12 |
| 5,942,093 A | 8/1999 | Rakestraw et al. | 204/450 |
| 5,961,800 A | 10/1999 | McBride et al. | 204/450 |
| 5,997,746 A | 12/1999 | Valaskovic | |
| 6,004,443 A | 12/1999 | Rhodes et al. | |
| 6,012,902 A | 1/2000 | Parce | 417/48 |
| 6,013,164 A | 1/2000 | Paul et al. | 204/450 |
| 6,019,882 A * | 2/2000 | Paul et al. | 204/450 |
| 6,045,933 A | 4/2000 | Okamoto | 429/17 |
| 6,139,734 A | 10/2000 | Settlage et al. | 210/198.2 |
| 6,167,910 B1 | 1/2001 | Chow | |
| 6,221,332 B1 * | 4/2001 | Thumm et al. | 423/659 |
| 6,315,905 B1 | 11/2001 | Settlage et al. | 210/656 |
| 6,386,050 B1 | 5/2002 | Yin et al. | 73/861.95 |
| 6,402,946 B1 | 6/2002 | Spraul et al. | 210/198.2 |
| 6,404,193 B1 | 6/2002 | Dourdeville | 324/306 |
| 6,406,605 B1 | 6/2002 | Moles | 204/601 |
| 6,416,642 B1 | 7/2002 | Alajoki et al. | |
| 6,428,666 B1 | 8/2002 | Singh et al. | |
| 6,460,420 B1 | 10/2002 | Paul et al. | 73/861.52 |
| 6,477,410 B1 | 11/2002 | Henley et al. | 604/20 |
| 6,616,823 B2 | 9/2003 | Kopf-Sill | |
| 6,619,311 B2 | 9/2003 | O'Connor et al. | |
| 6,719,535 B2 | 4/2004 | Rakestraw et al. | 417/50 |
| 6,766,817 B2 | 7/2004 | da Silva | |
| 2001/0020589 A1 | 9/2001 | Kopf-Sill | |
| 2002/0017484 A1 | 2/2002 | Dourdeville | 210/198.2 |
| 2002/0022802 A1 | 2/2002 | Simpson | 604/186 |
| 2002/0070116 A1 | 6/2002 | Ohkawa | 204/603 |
| 2002/0072126 A1 | 6/2002 | Chervet et al. | 436/161 |
| 2002/0076598 A1 | 6/2002 | Bostaph et al. | 429/38 |
| 2002/0125134 A1 | 9/2002 | Santiago et al. | 204/450 |
| 2002/0189947 A1 | 12/2002 | Paul et al. | |
| 2002/0195344 A1 | 12/2002 | Neyer et al. | |
| 2003/0052007 A1 | 3/2003 | Paul et al. | |
| 2003/0138678 A1 | 7/2003 | Preidel | 429/13 |
| 2003/0190514 A1 | 10/2003 | Okada et al. | 429/31 |
| 2003/0215686 A1 | 11/2003 | DeFilippis et al. | 429/34 |
| 2004/0011648 A1 | 1/2004 | Paul et al. | 204/450 |
| 2004/0107996 A1 | 6/2004 | Crocker et al. | |
| 2007/0000784 A1 | 1/2007 | Paul et al. | |

FOREIGN PATENT DOCUMENTS

| | | |
|---|---|---|
| DE | 196 25 648 | 1/1997 |
| GB | 2 303 885 | 3/1997 |
| JP | 61237717 | 10/1986 |
| JP | 618964 | 3/1994 |
| JP | 09281077 | 10/1997 |
| WO | WO 96/39252 | 12/1996 |
| WO | WO99/16162 | 9/1998 |
| WO | WO 99/67639 | 12/1999 |
| WO | WO00/04832 | 2/2000 |
| WO | WO00/16937 | 3/2000 |
| WO | WO 00/43766 | 7/2000 |
| WO | WO00/55502 | 9/2000 |
| WO | WO 00/65337 | 11/2000 |
| WO | WO 2004/007080 | 1/2004 |

OTHER PUBLICATIONS

European Search Report, EP 02 73 9909.
Adamson, A.W. et al., *Physical Chemistry of Surfaces*, pp. 185-187 (Wiley, NY 1997).
Ananthakrishnan, V. et al., *A.I.Ch.E. Journal*, 11(6):1063-1072 (Nov. 1965).
Aris, R., *Proc. Roy. Soc.* (London), 235A:67-77.
Burgreen, D. et al., *The Journal of Physical Chemistry*, 68:5 1084-1091 (May 1964).
Carvalho, R.T. et al. *Applied Optics*, vol. 33, No. 25 (Sep. 1, 1994).
Chatwin, P.C. et al., *J. Fluid Mech.*, 120:347-358 (1982).
Desiderio et al., *Electrophoresis*, 20:525-528 (1999).
Doshi, Mahendra R. et al., *Chemical Engineering Science*, 33:795-804 (1978).
Drott, J. et al., *J. Micromech. Microeng.* 7:14-23 (1977).
Enoksson, Peter et al., *Journal of Microelectromechanical Systems*, vol. 6, No. 2 (Jun. 1997).
Gan, W. et al. *Talanta* 51:667-675 (2000).
Jessensky O. et al., *J. Electrochem. Soc.* 145(11):3735-3740 (Nov. 1998).
Johnson, David Linton et al., *Physical Review Letters*, 57(20):2564-2567 (Nov. 17, 1986).
Johnson, David Linton et al., *J. Fluid Mech.* 176:379-402 (1987).
Johnson, David Linton et al., *Physical Review Letters*, 37(7): 3502-3510 (Mar. 1, 1988).
Kobatake, Y. et al., *J. Chem. Phys.* 40(8):2212-2218 (Apr. 1964).
Kobatake, Y. et al., *J. Chem. Phys.* 40(8):2219-2222 (Apr. 1964).
LeBlanc, Jacques C., *Rev. Sci. Instrum.* 62(6), 1642-1646 (Jun. 1991).
Ma, Y. et al., *Microporous and Mesoporous Materials*, 37:243-252(2000).
McNair, H.M., *Journal of Chromatographic Science* (Aug. 1974).
Morrison, F.A. et al., *J. Chem. Phys.* 43:2111-2115 (1965).
Nakanishi, K. et al., *Journal of Crystalline Solids*, 139:1-13 (1992).
Paul, P.H. et al., *Micro Total Analysis Systems*, pp. 49-52 (1998).
Paul, P.H. et al., *Micro Total Analysis Systems*, pp. 583-590 (2000).
Peters, E C. et al., *Anal. Chem.* 69:3646-3649 (1997).
Philipse, A.P., *Journal of Materials Science Letters*, 8: 1371-1373 (1989).
Wijnhoven, J. et al., *Science*, 281:802-804 (Aug. 7, 1998).
Yzawa, T., *Key Engineering Materials*, 115: 125-146 (1996).
Zeng, S. et al., *Sensors and Actuators*, B 79:107-114 (2001).
Agilent Technologies: Agilent 1100 Series Capillary LC System, A one-vendor solution for highest sensitivity and robustness, 7 pp.
Davis, M.T. et al., *Am. Soc. For Mass Spectrometry*, 6:571-577 (1995).
Davis, M.T. et al., *Am. Soc. For Mass Spectrometry*, 8:1059-1069 (1997).
Langridge, J. et al., Presented at COMBIO, Canberra, Australia, Sep. 30-Oct. 4, 2001, 4 pp.
Langridge, J. et al., Presented at 19th Montreux Symposium, Montreux, Switzerland, Nov. 6-8, 2002, 4 pp.
Martin, S.E. et al., *Analytical Chemistry*, 72(18):4266-4274 (2000).
Stahl, D.C., *Am. Soc. for Mass Spectromtry*, 7:532-540 (1996).

Vissers, J.P.C. et al., *Am. Soc. for Mass Spectrometry*, 13:760-771 (2002).

Office Action for U.S. Appl. No. 09/942,884 mailed on Apr. 22, 2004, 5 pages.

Office Action for U.S. Appl. No. 09/942,884 mailed on Aug. 12, 2004, 9 pages.

Office Action for U.S. Appl. No. 09/942,884 mailed on Mar. 9, 2005, 7 pages.

Advisory Action for U.S. Appl. No. 09/942,884, mailed on May 24, 2005, 3 pages.

Office Action for U.S. Appl. No. 10/155,474 mailed on Jul. 13, 2005, 5 pages.

International Search Report for PCT App. No. PCT/US02/19121, mailed Jan. 3, 2003, 4 pages.

International Preliminary Examination Report for PCT App. No. PCT/US02/19121, mailed Mar. 7, 2003, 4 pages.

Office Action for U.S. Appl. No. 10/246,284, mailed Sep. 30, 2005, 6 pages.

Office Action for U.S. Appl. No. 10/246,284, mailed Jan. 27, 2006, 6 pages.

Office Action for U.S. Appl. No. 10/246,284, mailed Oct. 4, 2006, 5 pages.

Office Action for U.S. Appl. No. 10/246,284, mailed Jul. 16, 2007, 6 pages.

\* cited by examiner

FLOW CONTROL SYSTEMS

This application is the national stage of International Application Number PCT/US02/19121 and claims the benefit of application Ser. No. 10/155,474, filed May 24, 2002.

This invention relates to methods and apparatus for controlling the flow of fluids.

Precise control of fluid flow rates is often important. Known flow controllers which make use of pumps and valves, and mechanical feedback loops, suffer from problems. One problem is undesirable variation in the flow rate, particularly at low flow rates. Another problem is that mechanical changes are needed to provide different flow rates.

We have recognized, in accordance with the present invention, that these problems can be ameliorated by using a combination of hydrostatic pressure and electroosmotic flow to control the flow of a fluid. The term "hydrostatic pressure" is used herein to denote any form of pressure which will cause a fluid to flow. It is known that by applying a suitable electrical potential to a suitable conductive fluid in a suitable relatively non-conductive channel, it is possible to create an electroosmotic force which will cause the fluid to flow.

In a first aspect, this invention provides a method of causing a working fluid to flow from a first point to a second point, which method comprises applying a driving pressure to the working fluid at the first point, wherein at least part of the driving pressure is provided by a driving fluid whose rate of flow comprises
  (i) a hydrostatic component (i.e. a component whose size depends on hydrostatic pressure), and
  (ii) an electroosmotic component (i.e. a component whose size and direction depends on electroosmotic flow).

The term "working fluid" is used herein to denote a fluid which can be used by an operable device in its operation. Such devices include, for example, chromatographs (including gradient liquid chromatographs, which may be followed by mass spectrometry), chemical microreactors, and separation systems (including micro-separation systems), for example separation systems for chemical analysis, gene sequencing, and characterization of protein expression from biological materials. The "second point" in the method of the first aspect of the invention can be, for example, an inlet of an operable device. The "second point" is also referred to herein as a terminus.

In some embodiments, the driving fluid is the same as the working fluid. In other embodiments, the working fluid comprises a stored fluid which (i) is stored in a storage element (or "cartridge") at the first point, and (ii) is displaced from the storage element by the driving fluid. The apparatus can include a valving system such that, when all the working fluid has been displaced from the cartridge, a new, full, cartridge can be inserted into the system.

The size and/or direction of the electroosmotic component can be varied by changing the electrical potential and/or the electroosmotic fluid to which the electrical potential is applied. This is valuable because it means that the same apparatus can be used in a variety of situations without the need for mechanical changes. Thus the first aspect of the invention includes methods in which apparatus operating under a first set of conditions causes the working fluid to flow from the first point to the second point and through an operable device during a first time period, and thereafter the same apparatus operating under a second set of conditions causes the working fluid to flow from the first point to the second point and through an operable device during a second time period; the working fluid during the first time period being different from the working fluid during the second time period, and/or the operating conditions of the operable device during the first time period being different from the operating conditions of the operable device during the second time period, and/or the operable device during the first time period being different from the operable device during the second time period.

In particular embodiments of the invention, the driving fluid flow is produced by a process which comprises
  (A) supplying a stream of fluid by hydrostatic pressure, and removing some of the fluid from the stream by electroosmotic flow; or
  (B) passing a mixture of first and second fluids under hydrostatic pressure through a channel in which electroosmotic flow is generated in the mixture; or
  (C) mixing
    (i) a working fluid whose flow rate depends on a pressure which is partly or wholly hydrostatic, and
    (ii) a second fluid whose flow rate, before said mixing, depends on a flow which is partly or wholly hydrostatic
wherein a mixture is created that passes through a channel in which electroosmotic flow is generated.

In one example of method (C),
  (i) the working fluid
    (a) is supplied from a first source at a hydrostatic pressure $P_1$, and
    (b) passes through a first flow control element; and
  (ii) the second fluid
    (a) is supplied from a second source at a hydrostatic pressure $P_2$, and
    (b) before it is mixed with the first fluid, passes through a second flow control element.
The first flow control element has a conductance $k_1$, the second flow control element has a conductance $k_2$, and the channel has a conductance $k_3$; and $1+k_3/k_1$ is greater than $P_1/P_2$ and $1+k_3/k_2$ is greater than $P_2/P_1$.

Some embodiments of the invention comprise
  (a) monitoring at least one variable, for example by one or more of a pressure transducer, a flowmeter, a temperature sensor, a heat flux sensor, a displacement sensor, a load cell, a strain gauge, a conductivity sensor, a selective ion sensor, a pH sensor, a flow spectrophotometer, and a turbidity sensor, and
  (b) changing, in response to said monitoring, an electrical potential which generates at least part of the electroosmotic component.

In some embodiments of the invention, variations in the electroosmotic component at least partially compensate for variations in the hydrostatic component.

In some embodiments of the invention, the rate of flow of the driving fluid at the second point is less than 50, or less than 10, or less than 1, or less than 0.5, microliter/minute, and may be, for example, more than 0.1, or more than 0.2, microliter/minute.

In some embodiments of the invention, the working fluid has at least one of the following characteristics:
  (i) it comprises a liquid having an ionic strength of least 25 millimolar, for example, less than 0.5 millimolar;
  (ii) it comprises a liquid having a dynamic viscosity greater than 5 centipoise;
  (iii) it comprises a substantially pure organic liquid;
  (iv) it comprises a liquid having a dielectric constant less than 20;
  (v) it comprises a liquid containing polyvalent ions; and
  (vi) it comprises a liquid having a pH value less than 7, for example less than 4.

In a second aspect, this invention provides apparatus suitable for use in the method of first aspect of the invention, the apparatus comprising (1) a channel which includes an inlet and an outlet, and through which a fluid under pressure can flow from the inlet to the outlet;
(2) a porous dielectric material which is positioned within the channel between the inlet and the outlet; and
(3) electrodes which are positioned so that, when an electrokinetic fluid under hydrostatic pressure is flowing through the channel between the inlet and the outlet, the rate at which the fluid flows can be changed by changing an electric potential connected to the electrodes.

These three components together form what is referred to herein as an electroosmotic device or channel.

The apparatus preferably has at least one of the following characteristics:

(a) it comprises a flow control element through which a fluid under pressure can flow before reaching the inlet;
(b) it comprises a flow control element through which a fluid under pressure can flow after leaving the outlet;
(c) it comprises an operable device which
  (i) employs a pressurized fluid in its operation and
  (ii) is connected to
    (a) the outlet, so that when pressurized fluid flows from the outlet, it passes through the device, or
    (b) a first outlet of a conduit having a second outlet connected to the channel and an inlet which can be connected to a source of pressurized fluid;
(d) it comprises a first source for a first fluid and a second source for a second fluid, both the first source and the second source being connected to the inlet so that pressurized fluid from the sources can pass through the inlet into the channel;
(e) it comprises a variable power supply connected to the electrodes;
(f) it comprises at least one sensor for monitoring a control signal, and a feedback control mechanism operatively connected to the sensor, whereby, when the apparatus includes a power supply connected to the electrodes, the feedback control mechanism modulates the electric potential supplied by the power supply, for example so as to maintain the control signal within a predetermined range;
(g) it comprises a conduit having (i) a first conduit outlet which is connected to the inlet, (ii) a second conduit outlet which can be connected to an operable device or a plurality of operable devices, and (iii) a conduit inlet which can be connected to a source of pressurized fluid, whereby, when pressurized fluid enters the conduit, a part of the pressurized fluid flows through the channel and the remainder of pressurized fluid flows through the device or devices;
(h) it comprises two or more said channels and a conduit having (i) a plurality of conduit inlets connected to an inlet or an outlet of each of said channels, and (ii) a conduit outlet which can be connected to an operable device or a plurality of operable devices;
(i) it comprises two or more said channels, the dielectric materials in the channels being different from each other; and
(j) it comprises a power supply having electrodes connected to the channel through a bridge.

In the phrase "porous dielectric material" as used herein, the term "porous" is used to denote any material that is permeable to the fluid, and the term "dielectric" is used to denote any, material whose conductivity is substantially less than the fluid and has a finite permittivity. Examples of porous dielectric materials are a fused silica capillary, silica particles, an organic polymer, and products made by lithographic patterning, lithographic etching, direct injection molding, sol-gel processing, or electroforming. The term "flow control element" is used herein to denote a device through which a fluid under pressure can flow and which is such that the pressure of the fluid as it enters the device is greater than the pressure of the fluid as it leaves the device. The flow control element for example reduces the pressure by 5% or less, for example by at least 5%, for example by at least 10%, at least 20%, at least 30%, or at least 40% and by at most 80%, at most 60% or at most 50%. A flow control element is also referred to herein as "a flow element" or "a flow resistor". The apparatus of the invention can include one or more flow control elements, through which at least part of the driving fluid passes.

In a third aspect, this invention is directed to the use of electroosmotic flow to modify the rate at which a pressurized working fluid is delivered to an operable device which employs the pressurized fluid in its operation.

In a fourth aspect, this invention is directed to a flow controller system comprising:

(a) a first conduit having:
  (i) a first fluid inlet in fluid communication with a first fluid source at pressure $P_1$;
  (ii) a first fluid outlet at pressure $P_3$ in fluid communication with the first fluid inlet, wherein $P_3 < P_1$; and
  (iii) a first flow control element disposed between the first fluid inlet and a first node; and
(b) a second conduit having:
  (i) a second fluid inlet in fluid communication with a second fluid source at pressure $P_2$, wherein $P_3 < P_2$;
  (ii) a second fluid outlet in fluid communication with the second fluid inlet and, at the first node, with the first conduit;
  (iii) a second flow control element disposed between the second fluid inlet and the second fluid outlet; and
  (iv) a third fluid outlet at pressure $P_4$, wherein $P_4 < P_1$ and $P_4 < P_2$, the third fluid outlet being in fluid communication at a second node with the second flow control element outlet;

wherein $\alpha_1 = \theta_1 v_1$, where $v_1$ is the internal volume of the first node and $\theta_1$ is the sum of apparent compressibilities within $v_1$, $\alpha_2 = \theta_2 v_2$ where $v_2$ is the internal volume of the second node and $\theta_2$ is the sum of apparent compressibilities within $v_2$, the first flow control element has a conductance of $k_1$, the second flow control element has a conductance of $k_2$, and wherein $\alpha_1/k_1 > \alpha_2/k_2$.

The hydrostatic pressures used in this invention can be produced in any way, for example by one or more pumps, for example high-pressure syringe pumps or hand pumps, or by air-driven systems.

One or more fluids can be passed through the electroosmotic channel. In one embodiment in which two fluids are passed through the channel, the channel has a fluid inlet (i.e. an inlet for fluid) that is in fluid communication with a first fluid source (i.e. a source of a first fluid) and a second fluid source (i.e. a source of a second fluid), which are at pressures $P_1$ and $P_2$, respectively. The channel also has a fluid outlet (i.e. an outlet for fluid) that is in fluid communication with the fluid inlet and a fluid terminus (i.e. a terminus for fluid) at pressure $P_3$, also referred to as outlet pressure. The outlet pressure is less than both $P_1$ and $P_2$. The channel is electrokinetically active when a power supply applies a suitable electrical potential to the electrodes. The electric potential generates an electroosmotically-driven flow component that modulates at least one of the pressure driven flows. To limit the pressure and flow rates at different points in the system, flow restrictors can be provided at appropriate locations.

Optionally, two or more electroosmotic devices can be used in a system. For example, one device can control the ratio of the two fluids and the other can control the total amount of fluid flow (FIGS. 15a and 15b).

In some embodiments of the invention, electroosmotic fluid, i.e. fluid in which electroosmotic flow can be generated (which is also referred to herein as electrokinetic fluid), is provided with two flow paths, one which leads to the terminus, and the other to the electroosmotic device. By varying the potential of the electrodes of the electroosmotic device, varying amounts of the electroosmotic fluid flow to the terminus.

In some embodiments of the invention, a fluid storage element for storing electroosmotic fluid is placed immediately before the electroosmotic device and the electroosmotic fluid is forced into the device by a fluid under pressure.

In the foregoing disclosure of the invention, in the disclosure of the invention in the accompanying drawings, and in the disclosure of the invention below (including the description of the drawings) and in the claims, reference is made to particular features of the invention. It is to be understood that the disclosure of the invention in this specification includes all possible combinations of such particular features. For example, where a particular feature is disclosed in the context of a particular aspect or embodiment of the invention, or a particular drawing or a particular claim, that feature can also be used in the context of other particular aspects, embodiments, drawings or claims, and in the invention generally.

The invention is illustrated in the accompanying diagrammatic drawings in which

Figure 1:
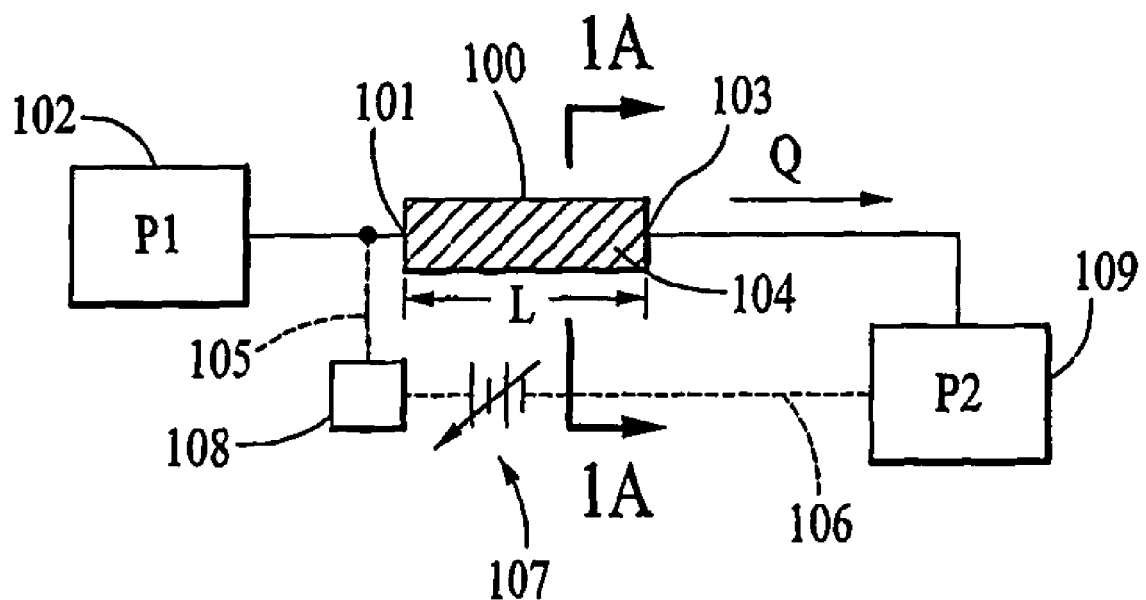
FIG. 1 illustrates an embodiment of the present invention.

The present invention utilizes principles of electroosmotic flow for fluid control purposes. Electroosmotic flow, also known as electrokinetic flow, can compete with or even dominate the flow that would otherwise be produced by application of a pressure difference across a channel. Electroosmotic flows in the present invention are generated using appropriate fluids and dielectric materials with application of an electrical field utilizing electrodes. The fluid provides a high zeta potential with respect to the porous dielectric material.

It is desirable that the magnitude of this zeta potential be in the range of about unity to 150 mV or greater. The zeta potential may be either positive or negative in sign. The sign and magnitude of the zeta potential are dependent on the dielectric constant of the fluid, the pH of the fluid, the ionic strength of the fluid and the type of ions in the fluid.

The fluid may be a pure fluid or a mixture of pure fluids that may have in addition some small concentration of a conducting species such as various ions. Preferably, the pure fluids should have high dielectric constant (between about 5 and 100 relative units), low dynamic viscosity (between about 0.1 and 2 centipoise) and low conductivity (between about $10^{-4}$ and $10^{-14}$ mho/m). Additives are preferably introduced to define or control the pH and ionic strength of the fluid. Additives should be of a kind and of a concentration to completely dissolve in the fluid. The kind and concentration of these additives preferably are chosen so as to enhance or optimize the zeta potential under the conditions imposed by the size of the pores in the porous dielectric medium.

Suitable pure fluids include by way of example, but not limitation: distilled and/or deionized water, cyclic carbonates, methanol, ethanol, 1-propanol, 2-propanol, 1-butanol, 1-pentanol, 1-hexanol, 1-heptanol, benzyl-alcohol, nitromethane, nitrobenzene, butanone, dimethoxymethane, dimethylacetamide, dioxane, p-dioxane, acetonitrile, formamide, methyl formamide, tetrahydrofuran, dimethyl formamide, acetone, acetic acid, triethylamine, dichloromethane, ethylene glycol, and dimethylsulfoxide.

To yield a zeta potential, generally, the surface of the dielectric material exhibits acidic or basic sites that become ionized in the presence of the fluid. These ionizable surface sites may be native to the material or may be the result or adsorption or grafting of some species onto the surface material.

Native ionizable materials include by way of example, but not limitation: silica (acidic), alumina (amphoteric), and Nylon (zwitterionic, carboxyl and amine). The sign of the zeta potential is the same as the sign of the net surface charge.

As an example of adsorption leading to surface charge, admixtures of polyethylene or polypropylene with ionic surfactants can be used. Polyethylene and polypropylene are non-polar polymers having no native ionizable sites. In an aqueous solution containing certain ionic surfactants (e.g. sodium dodecyl sulfate), the hydrophobic tail of the surfactant adsorbs to the polymer. The charged end of the surfactant then appears as a charge site on the surface.

The degree of ionization of the surface sites depends on the pH of the fluid. In most cases there is a pH at which the surface is net neutral and hence the zeta potential is zero. The zeta potential reaches a maximum value for pH values well above (for acidic surface sites) or pH values well below (for basic surface sites) the pH value at which the surface is net neutral. Ionizable surface sites can be added to a material by chemical reaction or grafting, or induced by creation of reactive surface chemistry or creation of defects via plasma or radiation treatment.

The dielectric material is selected for properties of: high zeta potential, sign of the zeta potential, insolubility and stability in the fluid with additives, low electrical conductivity, and sufficient mechanical strength.

Examples of suitable oxide materials include: silica, alumina, titania, zirconia, cerium oxide, lanthanum oxide, yttrium oxide, hafnium oxide, magnesium oxide, and tantalum oxide. These oxides may be amorphous or glassy or crystalline and may be combined in mixtures having other minor oxide components.

Examples of suitable glass materials include: crown or float or borosilicate glasses, lanthanum or flint or dense flint glasses, Pyrex™. Examples of suitable nitride materials include: silicon nitride, boron nitride, and aluminum nitride.

Examples of suitable polymers include: Nafion™ (Dupont Trade name, a sulfonated PTFE), polysulfone, polyethersulfone, cellulose acetate, mixed cellulose esters, polycarbonate, polyacrylonitrile, polyvinylidene fluoride, polyamide (Nylon), silicone elastomers, polymethacrylate, and nitrocellulose.

Other classes of suitable materials include certain semiconductors, carbides (e.g. titanium carbide) and sulicides (e.g. germanium silicide).

Counterions are ions in the fluid that have a charge sign opposite the sign of the zeta potential. Increasing the concentration of counterions in the bulk fluid tends to shield the surface charge and thus reduces the magnitude of the zeta potential. As an example, when silica is the dielectric material exposed to water at pH 7 as the pure fluid and KCl is used as an additive, the zeta potential for this system is negative with magnitudes of about: 120 mV, 100 mV, 70 mV and 30 mV for KCl concentrations of 0.1, 1, 10 and 100 millimolar, respectively. The valence of the counterion may also have a pronounced effect on the character of the zeta potential. Polyvalent (i.e. multiply charged) counterions may bind to the surface sites thus changing the pH of zero net charge (i.e. the "isoelectric point"). For example, silica in the presence of a singly valent counterion (e.g. $Na^+$) displays an isoelectric point of about 2.8, whereas silica in the presence of a bivalent counterion (e.g. $Ca^{2+}$ or $Ba^{2+}$) displays an isoelectric point in the range of 6 to 7. In this regard, the transport fluid preferably is selected or purified to be substantially free of polyvalent counterions.

The ionic additives that can be added to the fluid may be broken into two general classes: those that fully ionize (e.g. salts, strong acids and strong bases) and those that partially ionize. The former class can be employed primarily to establish the ionic strength of the fluid. The latter class can be employed primarily to buffer the fluid and thus establish and maintain the pH of the fluid. The two classes often are used in conjunction. The buffering species can exist in polyvalent states (e.g. formate exists as neutral or singly charged whereas phosphate exists as neutral, singly, doubly and triply charged). Thus the choice of a buffering compound is made in view of the issue of polyvalent counterions discussed above.

Examples of ionic and buffering additives include but are not limited to: alkali-halide salts, mineral acids and bases, organic acids and bases, phosphates, borates, acetates, citrates, malates, formates, carbonates, chlorates, nitrates, sulfates and sulfites, nitrates and nitrites, ammonium-, methylammonium-, ethylammonium-, propylammonium-salts, BIS, MES, TRIS, TES, HEPES, TEA.

Certain compounds, sometimes referred to as anti-static agents, are known to alter or eliminate the zeta potential. For example special agents are added to hydrocarbon fuels to eliminate zeta potentials and thus prevent static buildup during pumping and transport. As a further example, special agents are added to shampoos and conditioners again to eliminate the zeta potential and prevent static buildup. Certain surractants represent one class of these agents. In this regard the fluid is selected or purified so as to be substantially free of agents that degrade or eliminate the zeta potential. As examples: addition of small quantities of the surfactant SDS (sodium dodecyl sulfate) is known to increase the zeta potential of silica in aqueous solutions. The effect of the surfactant CTAB (cetyl trimethylammonium bromide) on silica in water is to reduce the zeta potential upon addition at low concentrations, to a value near zero as the concentration is increased, and to reverse the sign of the zeta potential at even higher concentrations. Addition of polyamines is also known to reduce or reverse the zeta potential of silica. Surface modification properties of surfactants are reviewed by M. J. Rosen, 'Adsorption of surface-active agents at interfaces: the electrical double layer,' Chapter II in, *Surfactants and Interaction Phenomena* (Wiley, NY, 1986), pp. 33-107.

The region of net charge in the fluid and adjacent to the dielectric surface extends some distance into the fluid. The one-on-e (1/e) thickness of this layer is approximately the Debye length in the bulk fluid. The Debye length at a temperature of 20° C. has a value of about 0.034 nm times the square root of the ratio of the fluid dielectric constant to the fluid ionic strength (the later taken in units of mols/liter). For one millimolar KCl in water the Debye length is about 9.6 nm.

Pores in the porous dielectric material vary in size along the length, and a variety of pore sizes may be present. Thus the dielectric material, saturated with a fluid at some given ionic strength, may have some subset of pores that contain substantially overlapped regions of net charge (here termed 'nanopores') with the balance of the pores containing some amount of core fluid that is free of charge-layer overlap (here termed 'regular' pores). All of the pores will transport current and hence ionic species, but the nanopores transport flow at a greatly reduced rate compared to the regular pores. It is desirable to apply a current so as to create a flow with minimal alteration of fluid ionic composition. The presence of nanopores reduces the efficiency of this process and may also lead to substantial and performance-degrading ionic strength, composition, and pH gradients across the porous element.

The porous dielectric materials may be fabricated by a wide variety of methods, examples include but are not limited to the following:

(a) Packed particles where the particles may be glass or ceramic or polymers. The particles may be held in place (i.e. confined in the channel) by any method known in the art, including but not limited to end-frits or other mechanical restrictions, or by color weiling under pressure or chemical bonding.

(b) Synthetic porous opaline materials, such as those described in, for example, A. P. Philipse, 'Solid opaline packings of colloidal silica spheres,' J. Mat. Sci. Lett. 8 pp. 1371-1373 (1989), and porous materials created by using opalines as a template, as described in, for example, J. E. G. J. Wijnhoven and W. L. Vos, 'Preparation of photonic crystals made of air spheres in titania,' Science 281 pp. 802-804 (1998).

(c) Phase separation and chemical leaching of a glass, for example the Vycor process as applied to a borosilicate or other composite glass as described in, for example, T. Yazawa, 'Present status and future potential of preparation of porous glass and its application,' Key Engineering Materials,' 115 pp. 125-146 (1996).

(d) Solgel or aerogel process in silica, alumina, titania, zirconia and other inorganic-oxides or mixtures thereof.

(e) Zeolite and zeolite-like porous media as described in, for example, Y. Ma et al, 'A review of zeolite-like porous materials,' Microporous and Mesoporous Materials, 243-252 (2000).

(f) Phase separation of polymer—inorganic oxide solutions as carried out using, for example the SilicaRod process described in, for example, K. Nakanishi and N. Soga, 'Phase separation in silica sol-gel system containing polyacrylic acid I. Gel formation behavior and effect of solvent composition,' J. Non-crystalline Solids 139 pp. 1-13 (1992).

(g) Direct machining by lithography and etching, molding, casting, laser ablation and other methods known in the arts. Direct machining may be used to generate, e.g., regular or irregular arrays of microchannels or pillars fabricated from a material that, in combination with a desired pumping of transport liquid, gives rise to a zeta potential. Such microchannels or pillars may be used as the porous dielectric materials of embodiments of the present invention.

(h) Porous polymers as prepared by film stretching, sintering, track etching, casting followed by leaching or evaporation, slip casting, phase inversion, thermal phase inversion. Like methods are often employed in the manufacture of polymer filter membranes. Porous polymer monoliths as described in, for example, E. C. Peters et al, 'Molded rigid polymer monoliths as separation media for capillary electrochromatography,' Anal. Chem. 69 pp. 3646-3649 (1997).

(i) Anodic etching as applied to silicon, as described in, for example, J. Drott, K. Lindstrom, L. Rosengren and T. Laurell, 'Porous silicon as tne carrier matrix in micro structured enzyme reactors yielding high enzyme activities,' J. Micromech. Microeng. 7 pp 14-23 (1997) or as applied to aluminum as described in, for example, O. Jessensky, F. Muller and U. Gosele, 'Self-organized formation of hexagonal pore structure in anodic alumina,' J. Electrochem. Soc. 145 pp. 3735-3740 (1998).

The porous materials may be fabricated in-channel or may be fabricated, possibly machined or cut, and then inserted or sealed into the channel. The surface properties may be altered before or after placement within a channel.

The sign and magnitude of the zeta potential can be altered or enhanced by modification of the surface or bulk chemistry of the porous material as described above. Modification of surface chemistry is generally done by reaction with sites (e.g. silanol, hydroxyl, amine) that are present on the native material. Modification of the bulk chemistry is generally done by synthesis of a material that directly incorporates ionizable sites. Examples include but are not limited to the following:

(a) Modification of the bulk chemistry of a polysulfone or polyethersulfone to convert some portion of the S=O groups to sulfonic acids.

(b) Modification of the bulk chemistry of PTFE to attach side chains terminated in sulfonic acid groups (Dupont product Nafion™).

(c) Modification of the bulk chemistry of a polyethersulfone or a polyvinylidene fluoride to introduce quaternary amines.

(d) Modification of the bulk or surface chemistry of a polyamide (Nylon) to provide a material with only carboxy (acidic) or amine (basic) surface sites.

(e) Modification of a zwitterionic material (e.g. Nylon) to terminate one of the existing ionizable sites with a nonionizable end group. The material is then converted to one having only a basic or an acidic site, rather than one having both types.

(f) Activation of a polymer material by introduction of defects or creation of cross-links via exposure to a plasma, ultraviolet or ionizing radiation.

(g) Modification of surface silanol groups with methoxy- or chloro-silanes to create amino groups or sulfonic acid groups.

Additional features of the invention are disclosed in the following description and discussion of the accompanying Figures. It is to be understood that these Figures are illustrative embodiments and do not limit the scope of the invention.

Figure 1A:
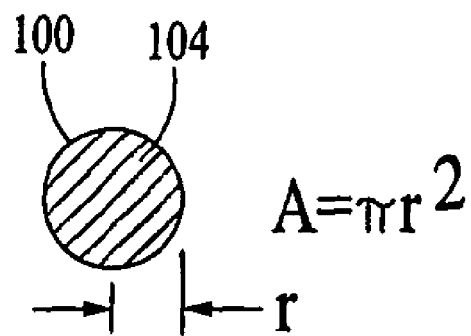
FIG. 1a illustrates a cross-section on line 1A of FIG. 1 and shows a channel filled with a porous dielectric material.

FIG. 1 illustrates an "in-line" or "series type" flow controller embodiment of the invention. With respect to FIGS. 1 and 1a, a channel 100 of total cross-section A and of total length L is packed with a porous dielectric medium 104. The channel 100 has an inlet 101 that is in fluid communication with a fluid source 102 at pressure $P_1$ and an outlet 103 at pressure $P_2$, where $P_2<P_1$. Throughout this description, we have assumed negligible resistance to fluid flow (and so negligible pressure drops) between the fluid source 102 and the inlet 101, and between the fluid outlet 103 and the fluid-collection reservoir 109. Under such circumstances, the pressure drop $\Delta P$ across the channel 100 is equal to $P_2-P_1$. One of skill in the art will have no difficulty, having regard to his own knowledge and the information contained in this specification, in modifying the equations below to account for pressure drops between the fluid source 102 and the inlet 101, and between the fluid outlet 103, and the fluid collection reservoir 109 by adjusting the term $\Delta P$ so that it accurately reflects the pressure drop across the channel 100. The flow rate Q is produced by the combined action of a potential difference $\Delta V$ generated by power source 107, and applied to the fluid within the channel through spaced electrodes 105, 106, and a pressure difference $\Delta P$ between the channel inlet 101 and the channel outlet 103.

With reference to FIG. 1, the porous dielectric material 104 is contained in a fluid-impermeable 'channel' 100. Channel materials are selected to meet requirements for mechanical strength, dielectric breakdown strength, transport fluid and fluid additive compatibility, and the capacity to retain the porous dielectric material 104. The geometry of the channel 100 covers the entire range from long in length and small cross section to short in length and large cross section. An example of the former geometry is a channel 100 that may be a capillary tube or a covered microchannel formed in a substrate having cross sectional shapes including round to rectangular to rectangular with sloped or curved sides. This channel 100 may be formed by any of the means known in the art. An example of the latter geometry is a large diameter and thin porous membrane.

The choice of pore size, topology numbers and physical geometry (e.g. porous element thickness and cross-sectional area) are particular to a given application. This then drives the needs for ionic strength and buffering capacity. In general, the following considerations may be taken into account for practicing preferred embodiments of the present invention.

(a) Use of singly valent counterions for a well-defined hence well-behaved zeta potential.
(b) Absence of compounds in the fluid that degrade or eliminate the zeta potential.
(c) Use of the lowest concentration of ionic species compatible with 'minimal' double layer overlap (i.e. a concentration yielding a fluid Debye length that is less than about one-fifth the characteristic pore size).
(d) Use of the lowest concentration of buffering ionic species consistent with establishing and maintaining the pH of the fluid.
(e) Use of ionic species that are compatible with, well soluble, and well dissociated in the fluid.
(f) A pore size distribution that is preferably monodisperse and if polydisperse does not contain occasional large pores or defects (e.g. cracks or voids) and contains no or a minimal number of 'nanopores'
(g) Use of a porous dielectric material 104 that is less conducting than the fluid with additives.
(h) Use of a porous dielectric material 104 with a dielectric strength sufficient to withstand the potentials applied without dielectric breakdown.
(i) Use of a porous dielectric material 104 that is mechanically strong enough to withstand the pressures applied both as regards the ability to withstand compression and collapse, and the ability to remain attached to the material of the bounding channel.
(j) Use of a porous dielectric material 104 that is resistant and insoluble in the transport fluid with additives.
(k) Use of a channel material that is an insulator, and in particular the channel material should be less conducting than the fluid with additives.
(l) Use of a channel material with a dielectric strength sufficient to withstand the potentials applied without dielectric breakdown.
(m) Use of a channel material that is mechanically strong enough and thick enough to withstand the pressures applied.
(n) Use of a channel material that is resistant and insoluble in the transport fluid with additives.
(o) Use of a fluid with a high value of the dielectric constant and a low value of the dynamic viscosity.
(p) Use of a combination of fluid, surface chemistry and additive ionic species chemistry that provides a high value of the zeta potential.
(q) Use of a fluid that is a pure fluid or a highly miscible mixture of pure fluids.

It is well-known to one of skill in the art that application of an electrical potential to a fluid via electrodes 105, 106 in that fluid can generate a current through the fluid, and that gas will be generated at the electrodes 105, 106 via electrolysis of the fluid. It is further appreciated that gas generation within a closed fluid channel may be undesirable. Thus, as shown in FIG. 1, a bridge 108 may be used to connect the electrodes 105, 106 in the fluid-filled reservoirs 102, 109 to the fluid in the channel 100. Such bridges are described, for example, in C. Desiderio, S. Fanali and P. Bocek, 'A new electrode chamber for stable performance in capillary electrophoresis,' Electrophoresis 20, 525-528 (1999), and generally comprise a porous membrane or porous solid selected to have sufficiently small pores so as to minimize fluid flow through the bridge, while at the same time to provide for the transport of ions (i.e. to allow current flow). Typical bridge materials include Nafion™ (an ion-selective polymeric membrane) or porous Vycor™ (a phase-separated and etched porous glass having a pore size on the order of 5 nm).

The flow rate in the channel 100 may be written as: $Q=(\nu \Delta V - \kappa \Delta P)A/LF$. This relation is a well-known combination of Darcy's law for pressure driven flow and the Helmholtz-Smoluchowski relation as adapted for electroosmotic flow in porous media. Here $\nu$ is the effective electroosmotic mobility, $\kappa$ is the Darcy permeability of the porous Media multiplied by F and divided by the dynamic viscosity of the liquid, and F is the formation factor of the porous media and is simply greater than or equal to the inverse of the connected porosity. F is by definition unity for a channel that does not contain porous media and takes values greater than unity for a channel containing porous media. The formation factor may be related to more common descriptors of porous media via $F=\tau^2/\phi$ where $\tau$ is termed the tortuoisty and $\phi$ is the connected porosity of the solid. The connected porosity is the wetted volume fraction that represents the through-connected pores and excludes dead-ended pores. Each of these descriptors may be determined using any of the methods well known in the art.

The Debye length scale can be altered by changing the ionic strength of the fluid and is preferably less than about one-fifth the characteristic pore size of the porous dielectric medium 104. For Debye lengths greater than about one-fifth the characteristic pore size, the charged layers on opposing walls of the pore begin to substantially merge having the effect of reducing the apparent zeta potential. For quantitative determination of the degree of double layer overlap the characteristic pore size, $D_{pore}$, is preferably taken as defined by D. L. Johnson and P. N. Sen, Phys. Rev. B 37, 3502-3510 (1988); D. L. Johnson, J. Koplick and J. M. Schwartz, Phys. Rev. Lett. 57, 2564-2567 (1986); and D. L. Johnson, J. Koplick and R. Dashen, J. Fluid Mech. 176, 379-392 (1987). This definition of $D_{pore}$ produces a strong weighting in favor of the larger through-pores in a porous medium.

Using the definition of $D_{pore}$ given above, the Darcy permeability is given by:

$$k_D = D_{pore}^2 M/F$$

where M is termed the 'pore geometry number', which equals $1/32$ for a circular tube and approximately equals $1/32$ for tubes of other cross sectional shapes and many porous media.

The effect of charge-layer overlap in simple geometries (e.g. slit or circular pores) has been studied theoretically. See, e.g., C. L. Rice and R. Whitehead, 'Electrokinetic flow in a narrow cylindrical pore,' J. Phys. Chem. 69 pp. 4017-4024 (1965); and D. Burgreen and F. R. Nakache 'Electrokinetic flow in ultrafine capillary slit,' J. Phys. Chem. 68 pp. 1084-1091 (1964). The conclusions of these studies can be applied analogously to a general porous medium through the use of $D_{pore}$ as defined above.

The effective electroosmotic mobility may be written as:

$$\nu = \in \zeta (1-\bar{\xi})/\mu$$

where $\in$ and $\mu$ are the dielectric permittivity and dynamic viscosity of the fluid, respectively, $\zeta$ is the zeta potential and ξ is a factor that provides for the effect of overlapping net charge layers (i.e. a reduction of the apparent zeta potential under conditions that the thickness of the charge layers becomes on the order of the size of the pores in the media). The zeta potential, hence the electroosmotic mobility, may be signed positive or negative depending on the nature of the fluid and the dielectric material (e.g. for a porous dielectric material 104 composed of $TiO_2$ saturated with an aqueous solution, the zeta potential will have a positive sign at low pH and a negative sign at high pH and will be negligibly small at the material iso-electric point which for $TiO_2$ is at about pH 6.2).

The electrokinetic property of an electrokinetically active element is characterized By $$a = \nu \Delta V / \kappa P_1$$

where $\Delta V$ is the voltage applied across the element. The quantity a is dimensionless and may be thought of as the electroosmotic flowrate produced by the potential $\Delta V$ divided by the pressure-driven flowrate produced by a pressure difference equal to $P_1$. A useful metric for the performance of an electrokinetically active material is the quantity $\nu/\kappa$, which has units of psi/volt. Using these definitions, the flowrates through elements may be appropriately summed at junctions and then solved for the pressures at the junctions.

The present invention employs a combination of pressure- and electroosmotically-driven flows in a channel 100 filled with a porous dielectric material 104. The applied potential preferably is selected to yield an electroosmotic flow in the same direction as the pressure-driven flow (e.g. for $TiO_2$ at high pH, hence a negative zeta potential hence a negative electroosmotic mobility, the potential would be applied with the negative terminal downstream with respect to direction of the pressure-driven flow). In this configuration the maximum flow rate through the channel 100 will be given by the flow rate equation above and only limited by the magnitude of the potential applied, whereas the minimum flow rate will be for purely pressure-driven flow that is with $\Delta V=0$, hence $Q=-\kappa \Delta PA/LF$. Thus the combination of pressure- and electroosmotically-driven flow in the channel 100 filled with the porous dielectric material 104 provides a voltage-controlled means to vary the flow rate through that channel. In effect, flow control is provided by varying the degree of electroosmotic 'assist' to the pressure-driven flow through the channel. As is explained in greater detail with respect to other preferred embodiments described below, sensors may be used to monitor parameters such as pressure, flow rate, etc. at one or more points in the flow controller system. Signals arising from these sensors may be used in a servo loop to maintain the signal within a predetermined range by adjusting the voltage outputted by the power supply in response to deviations between the signal and a predetermined set point.

Figure 2:
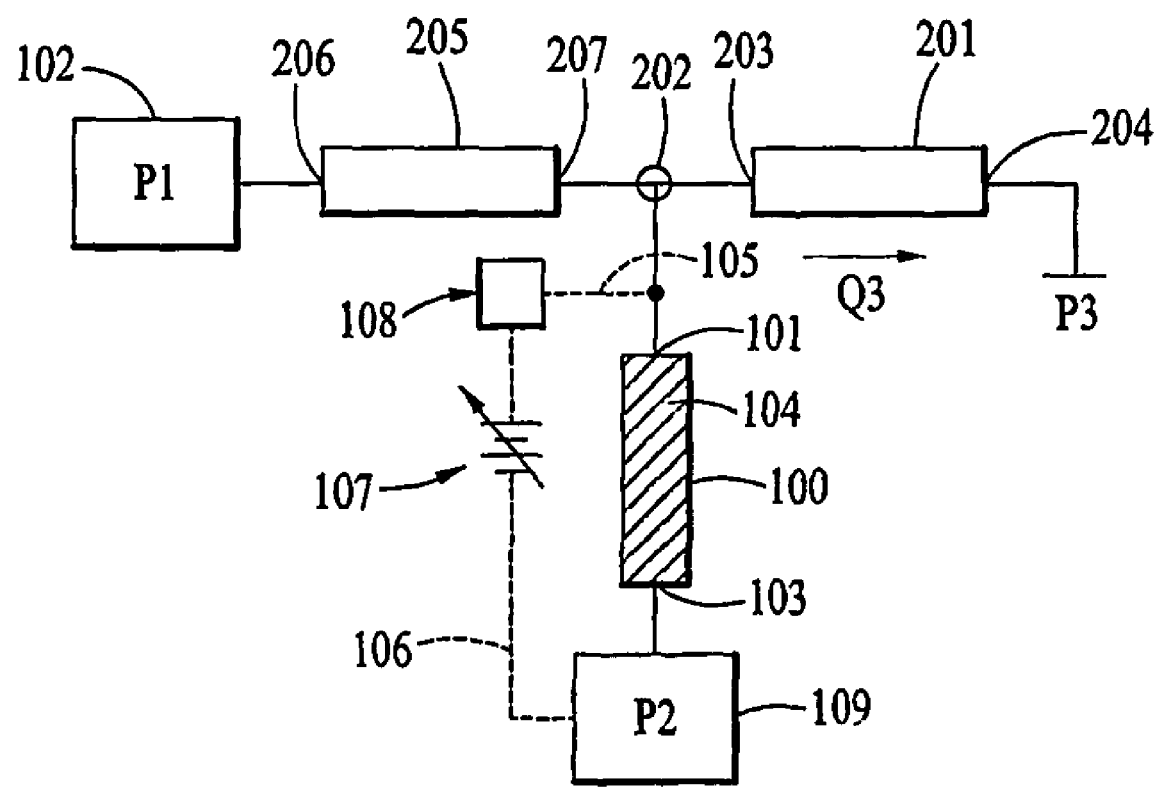
FIG. 2 illustrates a voltage-controlled flow splitter in accordance with an embodiment of the invention.

The system of FIG. 2 illustrates another preferred embodiment of the invention resulting in a device that acts as a voltage-controlled flow splitter. Fluid is supplied from a source 102 at a gauge pressure $P_1$ and subsequently split at a node 202 to flow through the device to a pair of fluid outlets 103, 204 at gauge pressures $P_2$ and $P_3$, respectively. Both $P_2$ and $P_3$ are less than $P_1$. The system of FIG. 2 may include a first flow resistor also referred to as a flow element 205 with an inlet 206 that is in fluid communication with the fluid source 102 at pressure $P_1$ and an outlet 207 in fluid communication with the node 202 at pressure $P_{node}$. The first flow element 205 can be included to provide a pressure-driven flow resistance, or Darcy flow resistance, between the fluid source 102 at pressure $P_1$ and the node 202 so as to reduce the flow rate and pressure available at $P_{node}$ such that the maximum available pressure and maximum available flow rate established at the node 202 is compatible with the electroosmotic flow rate of the channel 100. This is accomplished by making the resistance of the first flow element 205 to be some fraction or multiple of the flow resistances of the channel 100 and a third flow element 201 having an inlet 203 and an outlet 204.

The gauge pressure $P_2$ can be zero, that is, ambient pressure. However, this embodiment is not limited to this condition, which is provided purely for illustration of this application. The flow rate $Q_3$ through the third flow element 201, when $P_2=0$ is given by:

$$Q_3 = k_3(k_1 P_1(1-y) - (k_1+k_2)P_3)/(k_1+k_2+k_3)$$

If $k \equiv \kappa A/LF$ and $y \equiv (\nu_2/\kappa_2)k_2 \Delta V/k_1 P_1$.

The variable k can be considered effectively as the above-mentioned pressure-driven flow resistance parameter or conductance for each flow element or channel where A is the effective cross section area and L is the length of the element or channel. Thus for $\Delta V=0$, hence $y=0$, the flow rate through the third flow element 201 has a value of:

$$Q_3 = k_3(k_1 P_1 - (k_1+k_2)P_3)/(k_1+k_2+k_3)$$

whereas this flow rate $Q_3$ (i.e. the flow rate through the third flow element 201) is zero when:

$$y = 1 - (k_1+k_2)P_3/k_1 P_1$$

hence this flow rate is zero when the potential is set to a value of $$\Delta V = (k_1 P_1 - (k_1+k_2)P_3)(\kappa_2/\nu_2)$$

The flow rate $Q_3$ through the third flow element 201 can be made negative (i.e. the flow direction through the third flow element reversed) by the application of even higher values of the potential.

The Darcy flow resistance for the first flow element 205 is selected based upon on the desired range of flow rates through the third flow element 201 and the electroosmotic flow rate that is achieved when a maximum voltage is supplied across the channel 100 by the power source 107. For example, if one desires the ability to halt flow through the third flow element 201, $P_{node}$ must be equal to $P_3$. The pressure at the node 202 is given by: $P_{node} = (k_1 P_1(1-y) + k_3 P_3)/(k_1+k_2+k_3)$. Thus, the relative resistances of the first element 205 and the channel 100 should be designed to allow electroosmotic flow through the channel 100 to be equal to the pressure driven flow through the first flow element 205. Appropriate selections of relative flow resistances for the channel 100, the first flow element 205, and the third flow element 201 for a particular application are readily determined using the equations provided above by those skilled in the art.

Figure 3:
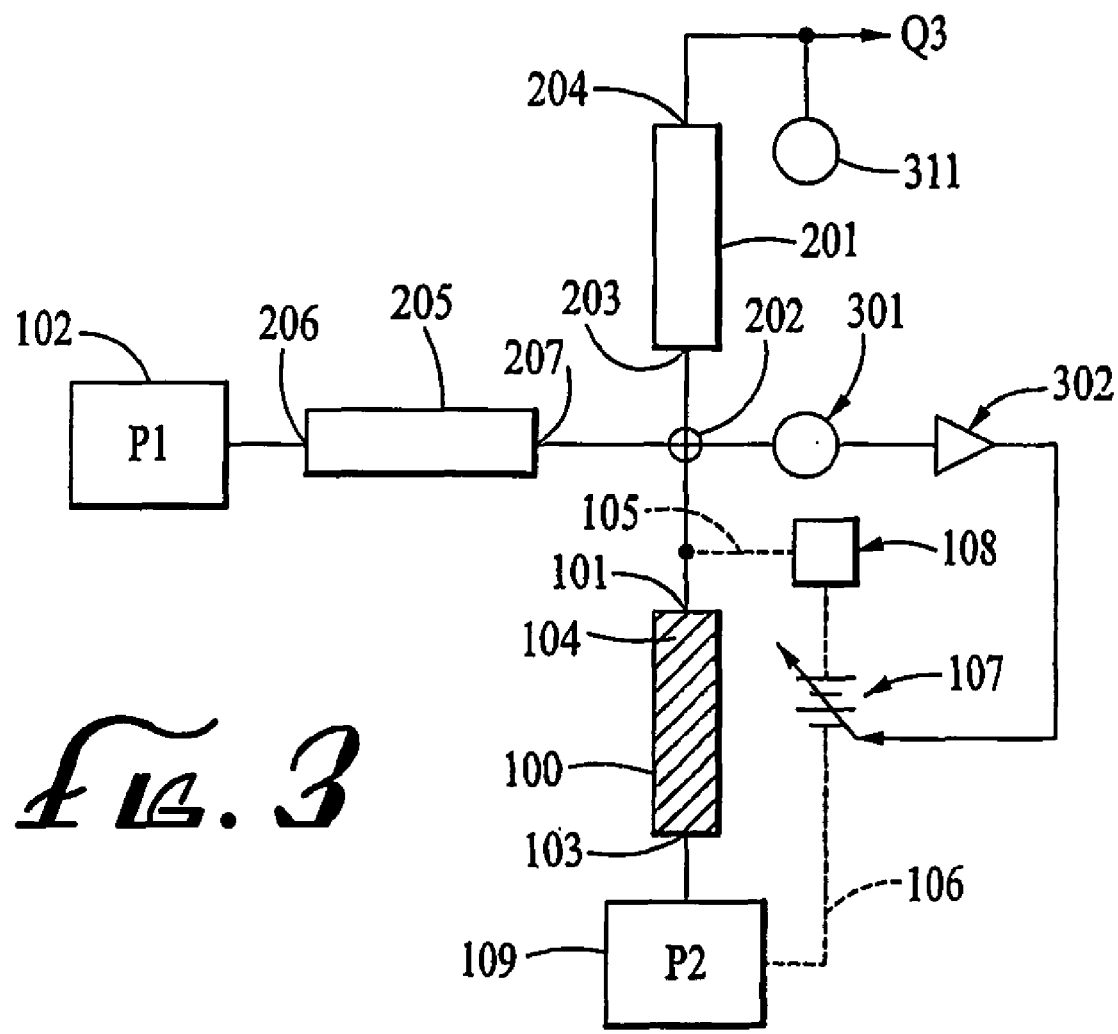
FIG. 3 illustrates an embodiment of the invention that includes a sensor and a servo loop controller for generating feedback signals and adjusting the power supply.

FIG. 3 illustrates an embodiment similar to that illustrated in FIG. 2, except for the addition of a first sensor 301 to monitor the pressure at the common node 202 of the flow elements shown in FIGS. 2 and 3. The first sensor 301 can be employed along with a servo loop controller 302 as part of a sense-and-control loop to regulate the pressure at the common node 202 and hence the flow rate, $Q_3$, through flow element 201. The flow rate $Q_3$ through the third flow element 201 also may be monitored directly or indirectly through a second sensor 311 as described in greater detail below. Such regulation may be desirable to compensate for variations in source pressure $P_1$ (resulting, for example, from fluctuations in the output of a pump providing the pressure $P_1$). Again referring to the example in which the gauge pressure $P_2$ is zero (and again not limiting the invention to this particular condition), the flow rate $Q_3$ through the third flow element 201 is given by $Q_3=k_3(P_{node}-P_3)$ where the pressure at the node 202 is given by:

$P_{node}=(k_1P_1(1-y)+k_3P_3)/(k_1+k_2+k_3)$. Thus variations in $P_1$ can be compensated by adjustments to $\Delta V$, hence y, so as to maintain a constant pressure at the node 202 and hence Is a particular flow rate $Q_3$ through the third flow element 201.

The control so achievable is limited by the condition that the pressure at $P_1$ remains sufficiently high to supply the required flow rate. This type of feedback control may be accomplished by any of the means that are well-known in the art, for example: observing a pressure or flow reading at the node 202 by use of the first sensor 301 and manually adjusting the potential applied by the power source 107; measuring the pressure or flow at the node 202 with the first sensor 301 and supplying this measurement to an analog electronic (or mechanical) servo loop controller 302 driving an electronically (or mechanically) adjustable power supply 107; measuring the pressure or flow at the node 202 with a first sensor 301 connected to a computer and using the computer to adjust the power supply 107, optionally, with higher order corrections applied (e.g. corrections for fluid or sensor temperature variations) in light of other data being supplied to the computer.

Multiple devices such as those illustrated in FIGS. 2 and 3, with or without servo-loop control, may be run in parallel to deliver multiple parallel sources of variable flow rate from one common source of fluid 102. The outlets of these parallel implementations need not but may terminate in loads at the same pressures. Similarly, the flow resistances and mobility coefficients of these parallel devices need not but may be the same.

The servo loop described above may employ a variety of control inputs and action outputs. By way of example, but not limitation, with the object of providing a constant flow rate $Q_3$ through the third flow element 201 the input to the servo loop is taken as, e.g., the differential pressure across the third flow element 201 (see FIG. 4, where the first and second sensors 301 and 311 may be used to measure pressure) or the differential pressure across some other passive pressure drop arranged in series with the third flow element 201. This differential pressure then provides a measure of the flow rate via Darcy's law. Alternatively, the flow rate may be detected by other means know in the art, such as but not limited to: a turbine flowmeter, a thermal convection flowmeter, a Doppler flowmeter measured at or beyond the fluid outlet 204 of the third flow element 201.

Figure 4:
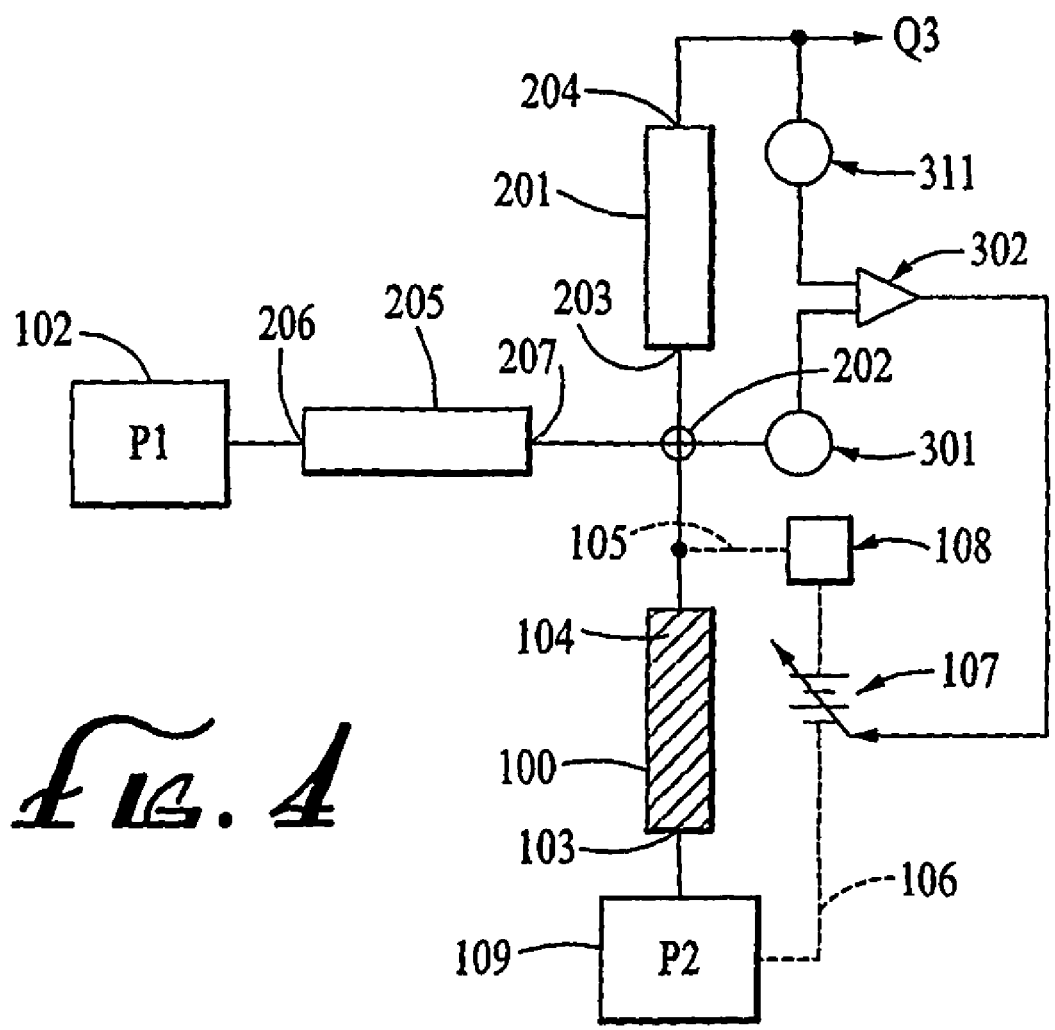
FIG. 4 illustrates an embodiment of the invention that includes two sensors and a servo loop controller for generating feedback signals and adjusting the power supply.

With the object to supply a flow rate of liquid used for heat transfer and by this the control of a temperature or heat flux as a result of the flow of liquid through the third flow element 201, the first and second sensors 301 and 311 (as shown in FIG. 4) may be used to measure temperature and the third flow element 201 is taken to be one side of a liquid heat exchanger or some further downstream element. For control of temperature the input to the servo loop may be a thermocouple or thermistor or RTD or other devices known in the art. For control of heat flux the input to the servo loop may be from a heat flux sensor or the temperature change of the fluid or other means known in the art.

Figure 5:
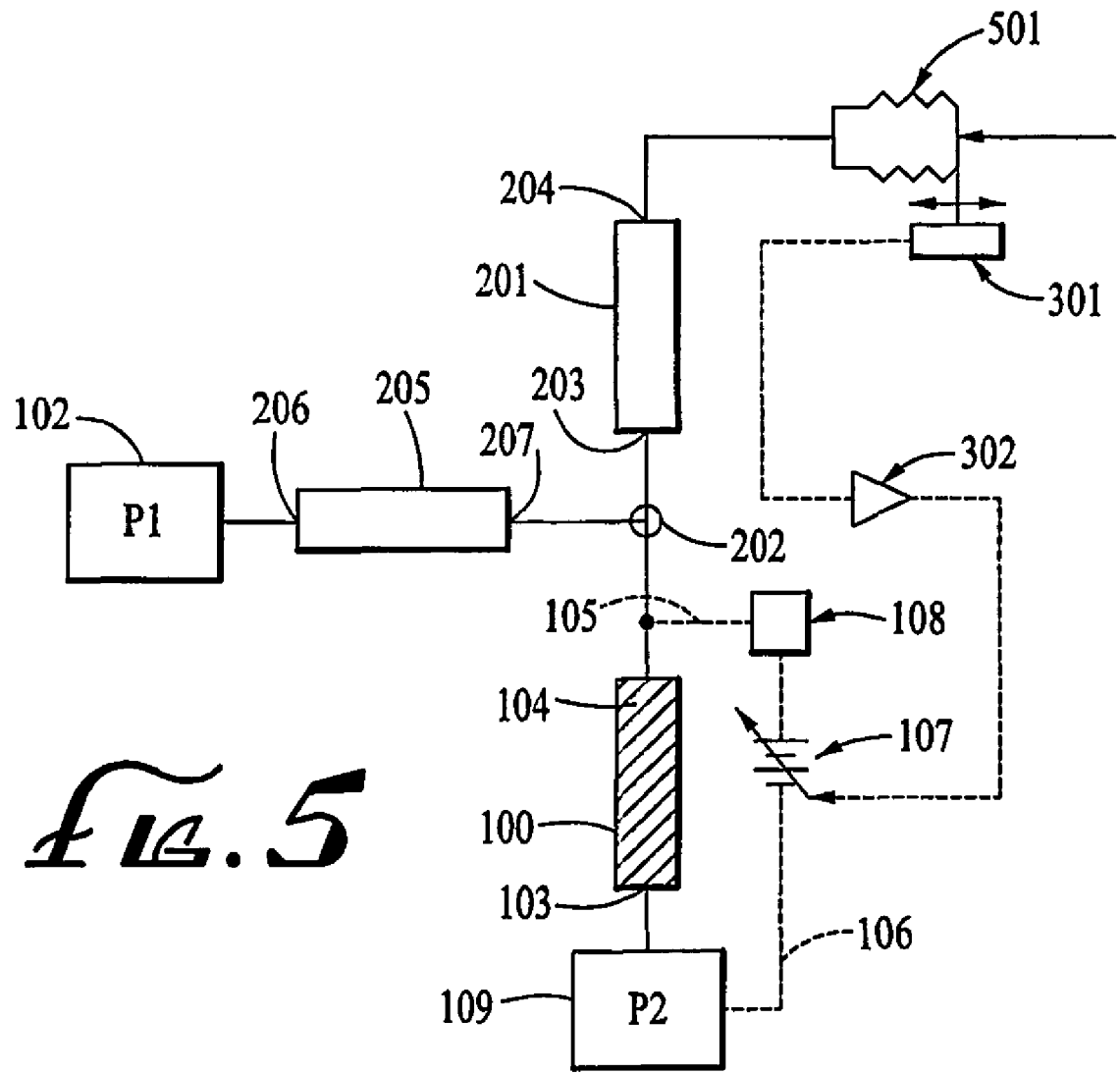
FIG. 5 illustrates an embodiment of the invention that includes a position or displacement sensor.

With the object of applying a mechanical force or displacement through the application of fluid pressure to a bellows 501 (see FIG. 5) or a piston or diaphragm or other means known in the art, the first sensor 301 may be used to generate a signal for input to the servo loop from a load cell (for force) or a displacement sensor as known in the art. One of skill in the art readily will appreciate that hydraulic mechanical systems are preferably applied under compressive load conditions. For the case where the load is naturally compressive (e.g. gravitationally or spring return loaded) a single flow control system may be used to apply and control the hydraulic force acting against the load. For this case the potential applied by the power supply 107 across the channel 100 is reduced to increase flow towards the load thus pushing against the load, whereas the potential across the channel 100 is increased to increase flow of fluid from the hydraulic actuator when the load is being returned. For the case where the load is neutral or where an active return force is required, two such flow control/servo systems may be used in a push-pull configuration.

The designs represented in FIGS. 1 through 5 illustrate several embodiments of the invention. It will be appreciated by those of skill in the art that these embodiments may be combined in a variety of series and parallel arrangements dictated by the problem or application at hand. In this regard, the embodiment illustrated in FIG. 1 may be considered as a form of in-line or series flow controller and the embodiments illustrated in FIGS. 2 through 5 may be considered forms of shunt or bleed flow controllers.

Figure 6:
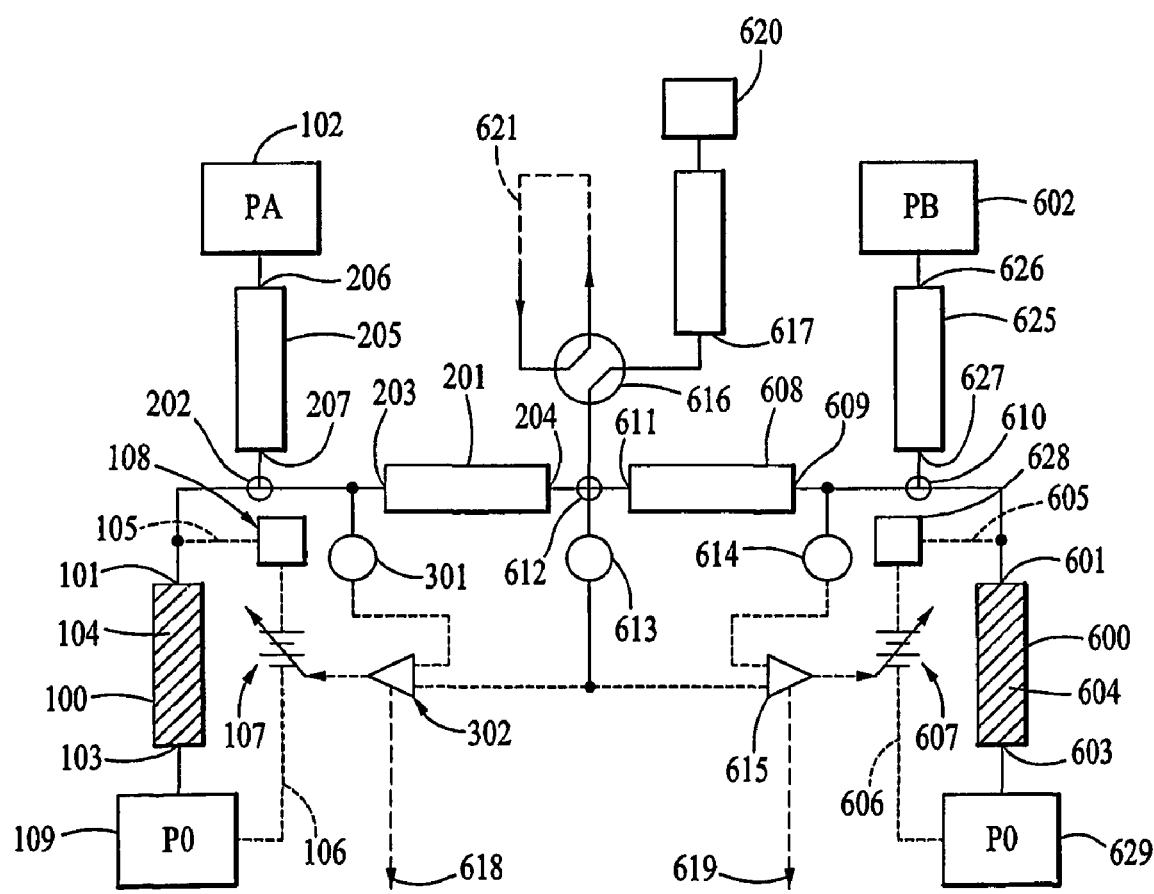
FIG. 6 illustrates an embodiment of the invention used to control the flow of two fluids. This embodiment can be used for generating fluid mixtures and gradients of the fluid mixtures for use in separations technologies.

The system illustrated in FIG. 6 shows a further embodiment of the invention useful for metering two fluids into a common stream. As one possible application and to illustrate this embodiment, such a system could be used to perform controlled mixing of two reagents or buffers to be used for gradient-type high-pressure liquid chromatography (HPLC). As described above, the use of pressure sensing and servo-feedback control may be applied (as shown in FIG. 6) to monitor and/or control and/or regulate both the mixture and the output flow rate. Again this system and the invention are not limited to this particular example.

In the example of FIG. 6 sources of two fluids, A, and B, 102, 602, at gauge pressures PA and PB, are fed to two shunt-type controllers (having flow elements 100, 205, 201, 600, 608 and 625 that have inlets 101, 206, 203, 601, 626 and 609 and outlets 103, 207, 204, 603, 627 and 611, respectively, bridges 108 and 628, nodes 202, 610, and 612 and sensors 301, 614, monitoring node pressures $P_{2A}$ and $P_{2B}$ respectively) that feed fluid to a common junction 612 (at gauge pressure $P_3$ monitored by the sensor 613) where the fluids mix. This mixture is further supplied to sample injector 616 and then to a pressure-driven chromatographic column 617. For purposes of this illustration, the outlet pressure of the chromatography column 617 and of collection reservoirs 109, 629 for the second and fourth elements 100 and 600 are taken as ambient (however the invention is not restricted to these outlet pressures, nor by these outlet pressures being the same).

The objective in this version of the invention is to provide constant flow rate to the column 617 while providing a programmed variation in fluid composition. The flow rates of fluids A and B from their respective sources 102 and 602 are independently measured and servo-controlled by two sense-and-control loops involving the first, second and third sensors 301, 613 and 614, the first and second servo loop controllers 302 and 615, the first and second power sources 107 and 607, and set-point inputs 618, 619. The programmed variation in fluid composition may be in the form of a series of step changes, or in the form of a continuous ramp (i.e. a gradient) or any of the other forms known in the separation arts. In applications requiring more than two sources of fluid, attendant flow controllers and servo loops may be combined to provide for more complicated or broad ranging fluid composition variations. Such configurations can be run in parallel from common sources or fluids to be able to perform multiple separations in parallel.

For the purpose of this illustration, sample injection through a sample loop 621 connected to a sample injector valve 616 at the head of the separation column 617 is taken to be performed by any of the means known in the HPLC arts (e.g. by a specialized sample injection valve e.g. 616, or by electroosmotic/electrophoretic injection through a porous media). For the purpose of this illustration, the end-use of the separation is taken to be any of the end-uses known in the HPLC arts (e.g. such as analyte detection by a detector 620 that measures, e.g., laser-induced fluorescence, optical absorption, refractive index or electrochemical potential; collection of the separation components; input to a mass spectrometer or ICP or NMR spectrometers; input to a next stage of separation by HPLC or LC or electrochromatographies; or preparative HPLC).

Figure 7:
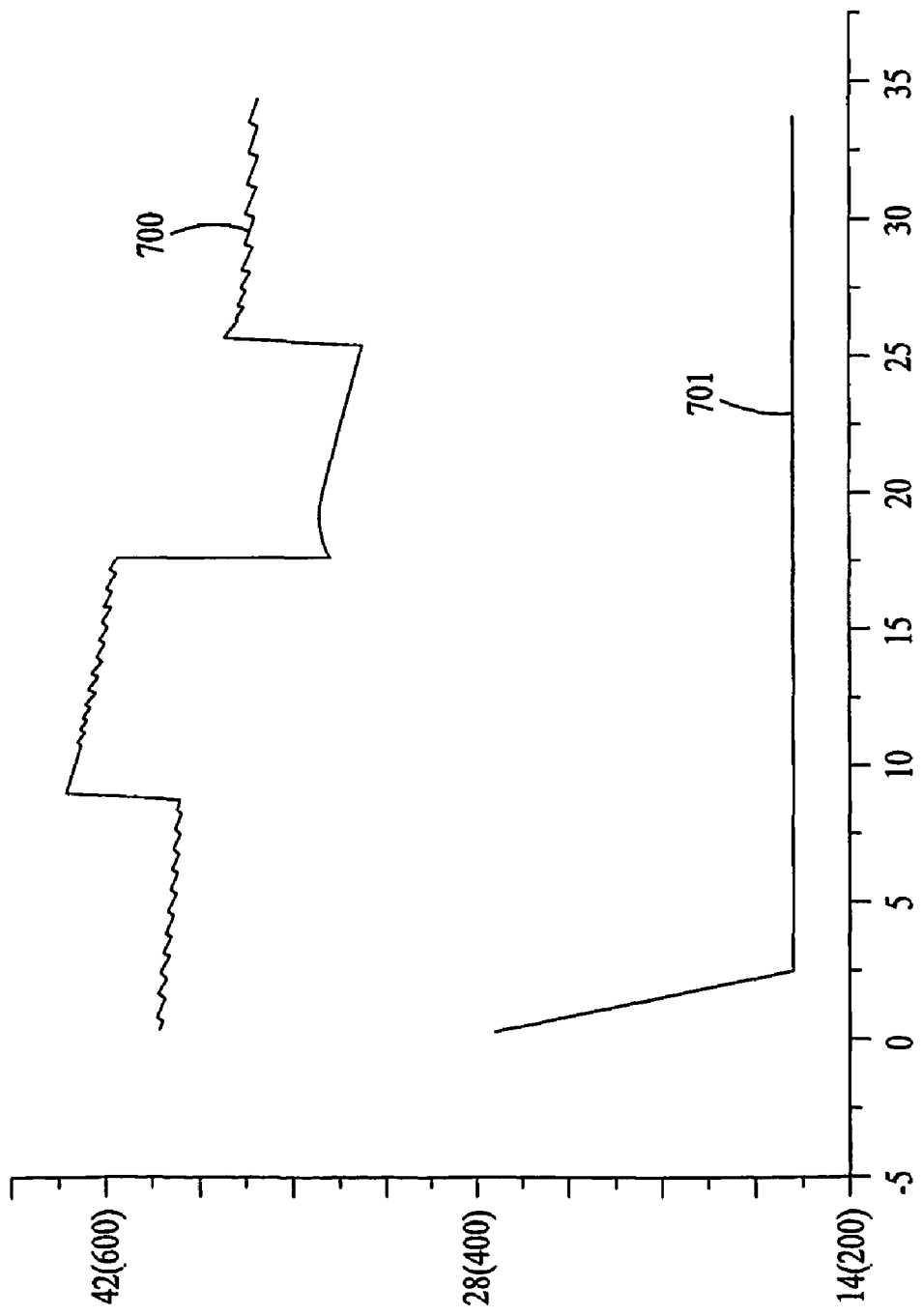
FIG. 7 illustrates controlled pressure generated by a flow controller of the invention despite varying driving pressure.
Figure 8:
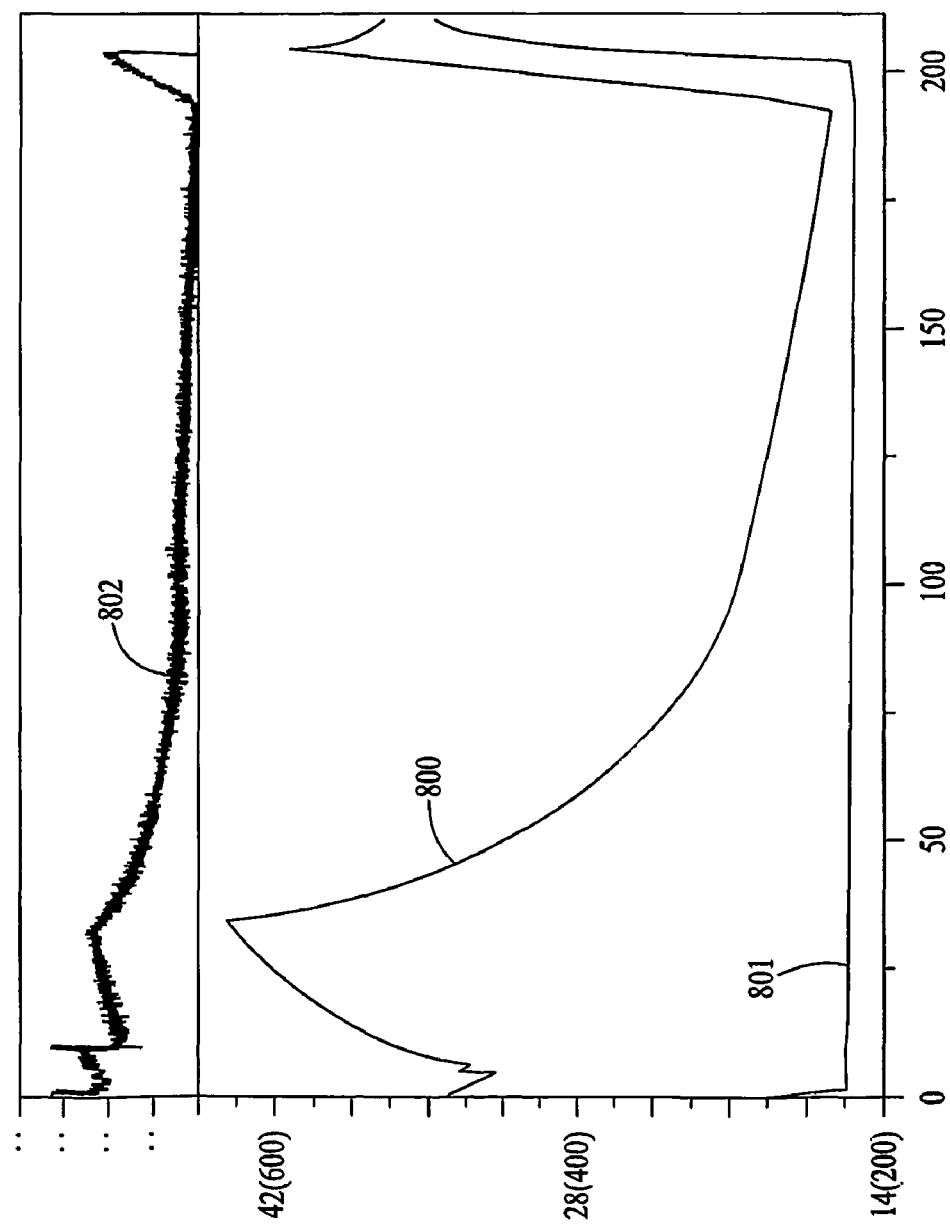
FIG. 8 illustrates controlled pressure generated by a flow controller of the invention despite decay in driving pressure.

FIGS. 7 and 8 show examples of flow control using the shunt-type flow controller configuration shown in FIG. 3. The flow elements were constructed from a section of 150 micron inner diameter silica capillary packed with 0.6 mm diameter non-porous silica beads. The flow elements, pressure transducers and pressure source were connected using conventional miniature HPLC fittings.

FIGS. 7-10 are plots of pressure (in psi) on the vertical axis against time (in minutes) on the horizontal axis.

The data shown in FIG. 7 were generated using a commercial "lead-screw" type syringe pump as the pressure source (the ripples on the driving pressure curve (line 700) correspond to the well-known pressure fluctuations produced by a syringe pump). A time t=0 the controller was switched on with a set point of ca. 225 psi. By t>2.5 minutes the set point was achieved as illustrated by a controlled pressure trace 701. Over the remainder of the test the feed rate of the syringe pump was changed several times, resulting in changes in the driving pressure 700 but the changes in the driving pressure 700 produced less than 2% variation in the controlled pressure 701. The driving pressure oscillations apparent in the trace 700 were effectively removed by the flow controller, and so are absent in the controlled pressure trace 701.

The data shown in FIG. 8 also were generated using a commercial "lead-screw" type syringe pump. Again at t=0 the controller was switched on and the controlled pressure 801 set point of ca. 225 psi was quickly achieved. In this example the driving pressure 800 was increased and the syringe pump then was switched off resulting in decay of the driving pressure 800 over a period of time. By ca. 190 minutes the driving pressure 800 had fallen to ca. 240 psi. whereas the controller maintained the controlled pressure set point of ca. 225 psi. Thus, flow control was achieved with a driving pressure only slightly greater than the set point pressure. The top trace 802 in FIG. 8 shows the current drawn through the flow control element.

Figure 9:
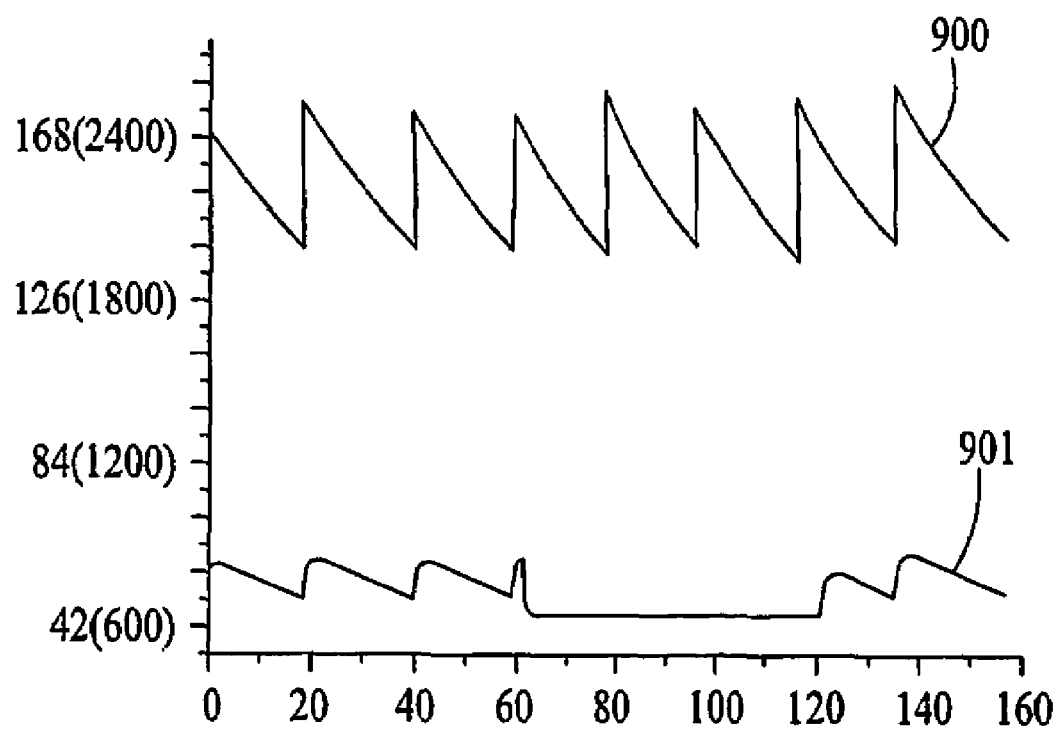
FIG. 9 is a graph showing driving pressure and column pressure as functions of time.

FIG. 9 shows pressure data from a nanobore capillary system driven by a traditional HPLC pump. The flow rate of the HPLC pump is monitored by a trace 900 showing that the pump output pressure is unstable in the microsystem causing 150 psi spikes. The output of a pressure transducer at the column head is shown by trace 901. Switching on the flow controller (between approximately 60 and 120 minutes) allows the pressure and flow rate to the column to be precisely controlled. Over the range where the flow controller operates the root mean squared ("RMS") variation in pressure around the 650 psi set point is 1.7 psi. At the 8.5 nL/sec flow rate in the column, this correlates to a RMS variation in flow rate of 0.02 nL/sec.

Since the set point of the flow controller can be changed to almost any value less than the driving pressure, two or more flow controllers may be combined to deliver fast, accurate, and reproducible gradients for use in microscale separations. A single pressure source can be used to drive all of the different fluids used in the gradient. Since the flow controller is a microscale device, it is compatible with being operated in a multiple parallel configuration.

Figure 10:
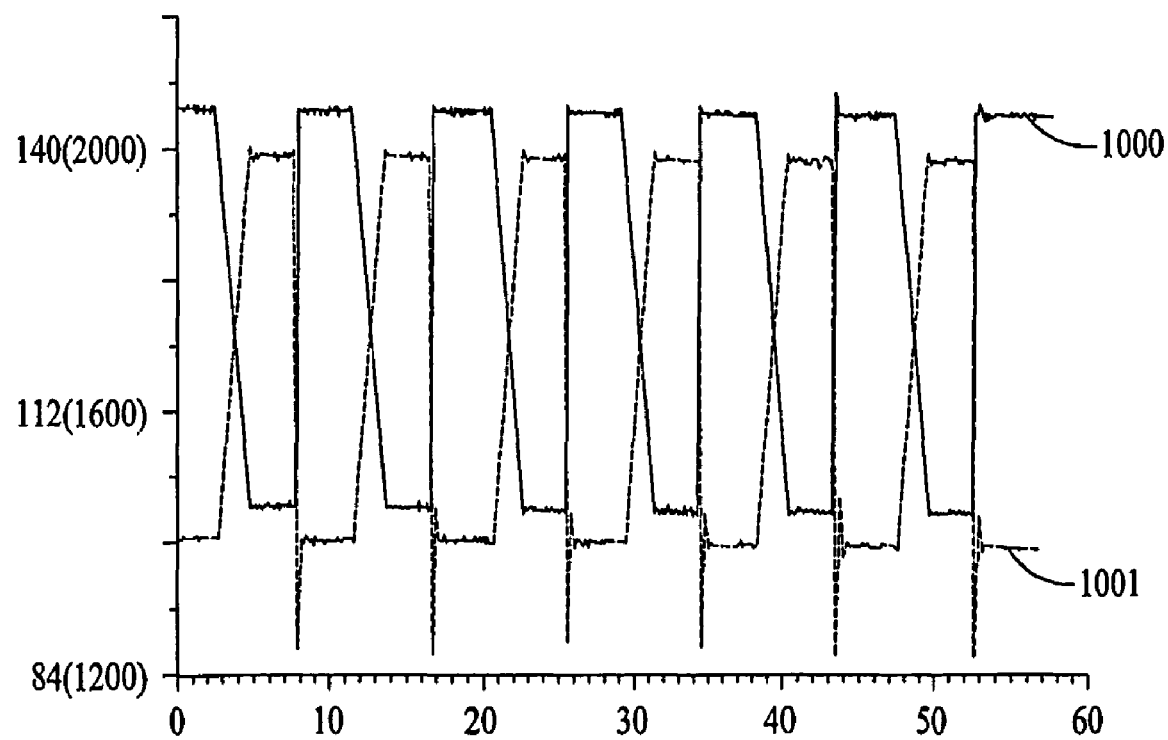
FIG. 10 is a graph showing reproducibility of water:acetonitrile gradients.

FIG. 10 shows the performance of a dual flow controller system such as the system illustrated in FIG. 6, programmed to generate water/acetonitrile gradients, illustrated in traces 1000 (water) and 1001 (acetonitrile). The traces 1000 and 1001 correspond to pressures measured at the nodes 202 and 610 illustrated in FIG. 6. Six gradients are repeated in the figure, starting at approximately 3, 12, 21, 30 and 39 minutes. The water and acetonitrile are both sloped several hundred psi from their starting to ending pressures over the 3-minute gradient and sent to a mixing tee at the head of the nanobore separation column. The gradient changes the composition of the mixed fluid while controlling the rate at which fluid is delivered to the nanobore separation column. The starting conditions of the gradient can be reestablished in less than 1 minute. In this system a simple hand-operated pump provides the driving pressure. The majority of the flow goes directly into the HPLC column; very little waste is produced. The flow rate in the separation column is compatible with feeding directly into a mass spectrometer. This demonstrates the ability of a dual flow controller system to quickly and reproducibly generate fast gradients in a nanobore HPLC system.

Figure 11:
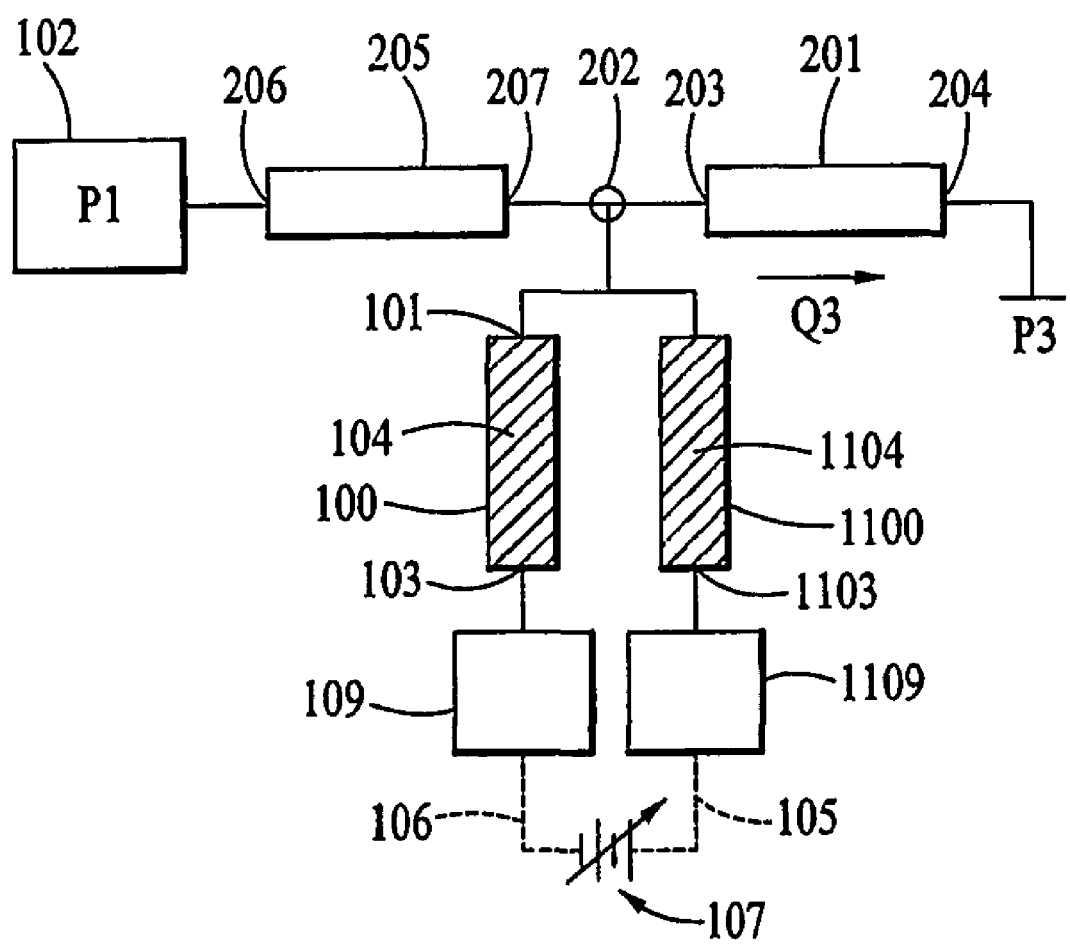
FIG. 11 illustrates an embodiment of the invention that provides a method to remove the electrode from the channel and an increased range of operating conditions.

As noted above, the presence of a current-carrying electrode in a closed channel may produce undesirable side effects. Bridges provide one method of removing the electrode from the channel while still providing current. As also noted above, the zeta potential is a function of fluid composition and pH. As such, any given flow control porous element may operate under some limited range of fluid conditions. FIG. 11 shows an embodiment of the invention that provides both a method of removing the electrode from the closed channel and increasing the range of operating conditions.

In FIG. 11, the second flow control element channel 100 is replaced by two such channels in parallel 100 and 1100. The fluid outlets 103, 1103 of the two channels 100, 1100 are led into separate fluid reservoirs 109, 1109, both at the terminal pressure P2 that is less than source 102 pressure $P_1$. Power from the power supply 107 is supplied via electrodes 105, 106 in the reservoirs. Current is then carried from the power supply 107 through one channel (e.g. 100), back through the other channel (e.g. 1100) to the power supply 107. The common fluid connection of the channels, the node 202, may then be held at an arbitrary potential (preferably but not necessarily system ground). The channels 100 and 1100 comprise different zeta potential porous dielectric materials 104, 1104 having pore sizes sufficiently large to support electroosmotic flow. Note that this configuration reduces to the case of a bridge in the limit that one of the channels contains material having a pore size too small to support electroosmotic flow but large enough to still carry a current.

For example, the material 104 in channel 100 may be silica with a nominal iso-electric point of pH 3 and the material 1104 in channel 1100 may be alumina with an iso-electric point of pH 9.2. As a further example, the material 104 may be modified to display a sulfonic acid group (nominal iso-electric point of pH 1.5) and the media 1104 may be modified to support a quaternary amine (nominal iso-electric point higher than pH 14). For a fluid with a pH between the iso-electric points of the two materials the electroosmotic flow through one channel will be towards the supply anode and the electroosmotic flow through the other channel will be towards the supply cathode. This then provides flow hence flow control over a wider range of pH conditions than could be supported using a single channel and at the same time removes the current-carrying electrodes 105, 106 from the closed channels 100, 1100.

As a specific example consider the materials 104, 1104 in channels 100 and 1100 to be silica and alumina, respectively. With fluid having pH 3 channel 100 filled with silica has a negligible zeta potential and thus does not provide electroosmotic flow, but still carries current. Channel 1100 filled with alumina has a high positive zeta potential with fluid having pH 3 and thus provides the electroosmotic flow (from the common junction 202 of the channels towards the supply anode) needed for flow control. With fluid having pH 9 the roles are reversed, the silica displays a high negative zeta potential whereas the alumina has a negligible zeta potential, thus the electroosmotic flow is through the channel 100 filled with silica, from the common junction 202 of the channels towards the supply cathode. For a fluid having a pH between 3 and 9, the channels 100 and 1100 both supply some degree of electroosmotic flow and thus contribute to the ability to achieve flow control.

It is apparent that the use of any given material as the active element in the embodiments of the invention described thus far restricts the range of liquids that may be used. For example, chromatography of many proteins and small molecules is performed under acidic fluid conditions. However, silica is not viable under acidic conditions. Hence, the embodiments of the invention thus far described may require a change in the electrokinetically active material to operate in different pH ranges.

In any case, the dynamic range of the flow controller is increased by increasing the zeta potential and decreasing the square of the effective pore size of the active element. The dynamic range of the embodiments thus far described may be not as great as desired because of the need to use a material that is compatible with a particular fluid.

The following embodiments may be used in conjunction with a much larger range of liquids. A primary application of the following embodiments is thus to chromatography where the working fluid is dictated by the type of separation.

Figure 12:
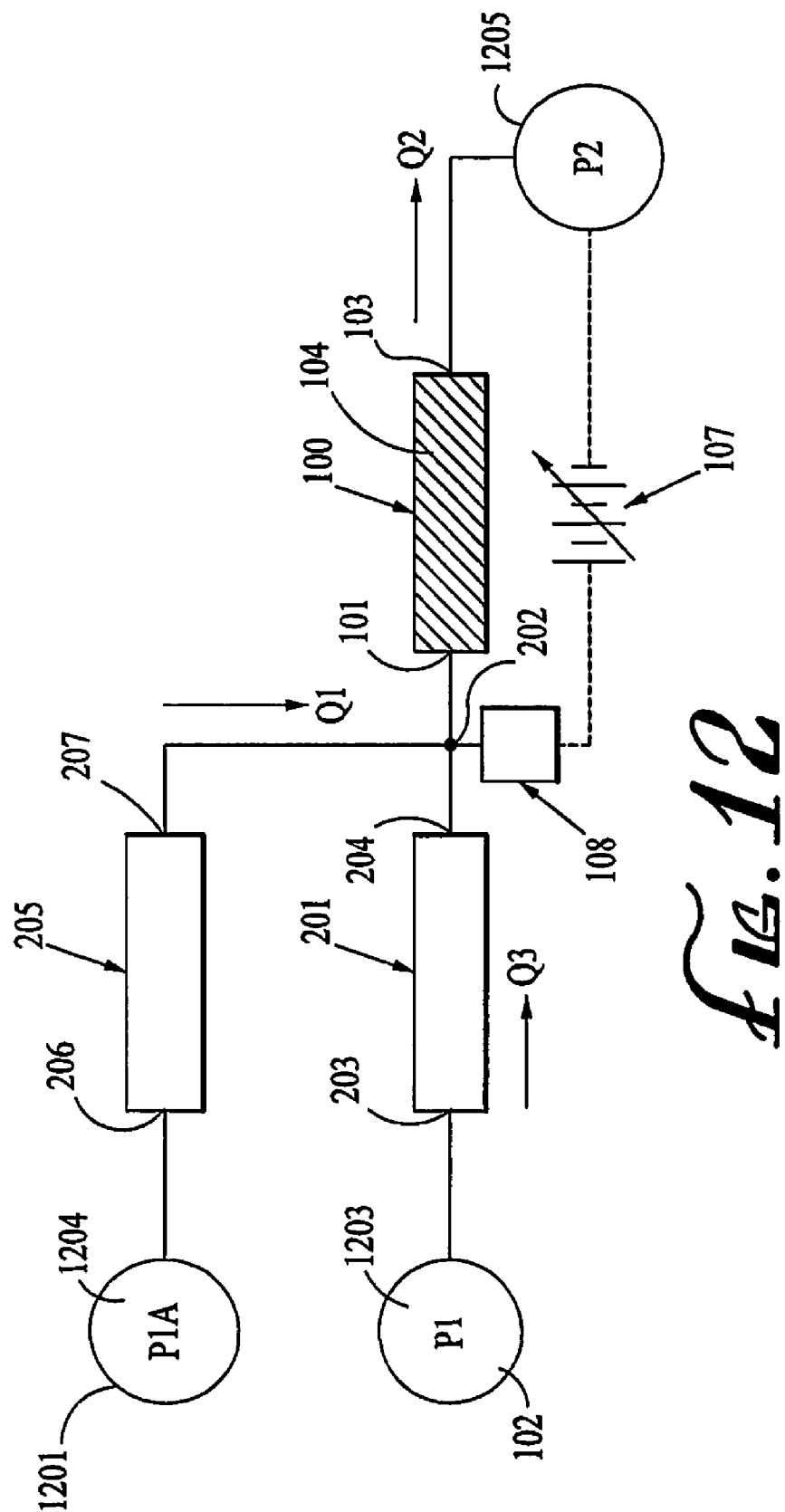
FIG. 12 illustrates a series-mode embodiment of the current invention wherein a second fluid is mixed with a working fluid to improve the performance and operating range of the electroosmotically-driven flow controller element.

The embodiment illustrated in FIG. 12 can be used in conjunction with a working fluid that does not, by itself, support electrokinetic activity. A working fluid 1203 from a source 102 at pressure P1 flows through the third flow element 201 to a junction 202 with the first and second flow elements 205 and 100, respectively. A second fluid 1204 from a second fluid source 1201 at pressure $P_{1A}$ flows through the first flow element 205 also to the junction 202. The second flow element 100 is electrokinetically active (i.e., the element exhibits a zeta potential and an external potential is applied to the element) and carries the mixture of the two fluids 1203 and 1204, respectively to a terminus 1205 at pressure P2 that is less than P1 and P1A. The configuration shown in FIG. 12 may be termed a series-mode configuration.

The second fluid 1204, supplied at pressure P1A, is not necessarily the same as the working fluid 1203. Rather the second fluid 1204 is intended to be mixed with the working fluid 1203 to alter the pH or ionic strength or fluid composition and thus provide for proper operation of the electrokinetically active second flow element 100.

If we again measure the pressures with respect to the $P_2$ gauge, the flowrate through the second element 100 is $Q_2 = ak_2P_1 + k_2P'$, where P' is the pressure at the junction 202, and the sign of a is arranged such that the electroosmotic flow is in the same direction as the pressure-driven flow through the second element. The sign of a is made positive by selecting the sign of the applied potential and the sign of the zeta potential such that the product is positive.

The flowrate through the third element is given by $$Q_3 = P_1 k_3 \frac{k_1 + k_2 - xk_1 + ak_2}{k_1 + k_2 + k_3}$$

where $x = P_{1A}/P_1$.

A set of conditions may be imposed to guide the selection of element conductances. Two conditions that may be imposed are setting $1 + k_2/k_1 > x$ and $1 + k_2/k_3 > 1/x$ to maintain both $Q_1$ and $Q_3$ positive for all positive values of a. Further conditions may be derived by requirements, if any, for the range of flowrates through the third element; the minimum being at no applied potential hence a=0, and the maximum can be a junction pressure of zero, hence $Q_{3 max} = k_3 P_1$. When the junction pressure is zero, $a = (k_3 + xk_2)/k_1$.

A further condition may be derived by requiring flowrates through the first and third elements that yield a mixture having properties suitable for high performance electrokinetics in the second element. The mixture of the two fluids may be characterized by the ratio of flowrates through the first and third elements, $Q_{13} = Q_1/Q_3$, given by:

$$Q_{13} = \frac{k_1}{k_3} \frac{xk_2 + xk_3 - k_3 + ak_2}{k_1 + k_2 - xk_1 + ak_2}$$

Those skilled in the art will have no difficulty, having regard to their own knowledge and the disclosure of this specification, in selecting and optimizing other sets of flow element parameters, given other design conditions.

The following example is for illustration purposes only and is not to be taken as a limitation of the invention. The working fluid can be aqueous 10 mM trifluoroacetic acid "TFA" yielding a pH of about 2.5. In this example, the second element employs silica as the active material, specifically a packing of nominal 0.6 micron non-porous silica beads yielding a performance of over 5 psi per volt under neutral to basic pH conditions. Silica displays little or no zeta potential at a pH of about 2.5. The second fluid is a mixture of 100 mM aqueous imidazole, a weak base with a pH of about 7.15, and 1 mM HCl. The HCl is not mandatory but is added to guarantee operation of the second element even running the pure second fluid.

The pH of the fluid entering the second element may be estimated, using well-established relationships, by solving:

$$(1+Q_{13})(C_H - K_w/C_H) + C_{TFA} + C_{HCl}Q_{13} - C_{IMD}Q_{13}/(1+K_{IMD}/C_H) = 0$$

for the H-ion concentration, $C_H$, hence the pH. Here $C_{TFA}$, $C_{IMD}$ and $C_{HCl}$ are the concentrations of TFA, imidazole and HCl in the first and second fluids, $K_w$ and $K_{IMD}$ are the equilibrium constants for water and imidazole, respectively.

For illustration, but not limiting the range of operation of invention, for the case of $P_1 = P_{1A}$, hence x=1, the ratio of flowrates is $Q_{13} = k_1/k_3$ for all values of a. A design using a value of $k_1$ that is 25% of $k_3$ provides a mixture that buffers the working fluid to about pH 7.2 at the inlet 101 of the second element 100. a condition that yields high performance electrokinetics from silica. A further advantage is gained in that the conductivity of the liquid mixture is substantially reduced, since the high mobility H-ions in the acidic liquid have been replaced by significantly lower mobility imidazole ions in the liquid flowing through the second element 100.

It will be appreciated, by inspecting the relationship for pH, that values of the product $C_{IMD}Q_{13}$ must be about two times greater than $C_{TFA}$ to obtain pH values greater than about 7. It is thus preferable to employ a concentrated weak-base in the second fluid (a concentration substantially higher than the acid concentration in the working liquid) to allow for the use of small values of $Q_{13}$. Obviously a strong base or a weak base with a very low equilibrium constant could be employed. However these in concentrated form yield a high pH second liquid that may damage materials. For example with 1 mM HCl and 100 mM aqueous tris(hydroxymethyl)aminomethane "TRIS" or imidazole, the pH values are about 10.4 or 9.15, respectively. The pH with the concentrated TRIS is sufficiently high to promote dissolution of silica. Whereas silica is reasonably stable at pH values less than about 9.5 making imidazole a viable candidate. Other weak bases may be equally employed.

Flow controller systems like the preceding embodiment of the invention, in which multiple fluids are used, can have one or more of the following advantages:

(a) The ability to run with a wider range of fluid compositions and fluid conditions using a single electroosmotically active element. The composition of the second fluid may be altered to address different working fluids but no change to the physical device/system is required.
(b) The ability to employ working fluids that are not suitable for electroosmotic flow. The mixture of the working fluid and the second fluid supports electrokinetic flow. Hence, the number of potential 'working' liquids includes those already discussed, but is also increased significantly. The working liquid preferably is miscible in and not reactive with the second liquid. For example, benzene, substituted benzenes, long chain aliphatics heptane, hexane, pentane, and carbon tetrachloride have relatively low permittivity and/or dipole moment and thus do not support electrokinetic flow. However these are miscible in isopropyl alcohol, for example, and the mixture can support electrokinetic flow.
(c) The ability to use silica as the electrokinetically active element with a much greater number of working fluids, and thus take advantage of a well-characterized, widely available, and easily formed material having high electrokinetic performance.
(d) The ability to use other high performance active materials (e.g. certain polymers or other metal oxides) under liquid conditions that provide for high performance and chemical stability of the materials.
(e) The ability to use silica as a negative zeta potential material at low working fluid pH values, which are often employed in running buffers in HPLC of proteins and small molecules.
(f) Electrokinetic operation over a well-defined range of pH, thus providing tolerance for and predictable operation with liquids bearing polyvalent ions.
(g) The ability to use a high ionic strength, hence high electrical conductivity, working fluid. The zeta potential, hence performance, decreases and the electrical power dissipation hence Joule heating increases with increasing ionic strength of the working fluid. In such cases the second fluid is preferably selected to be of low ionic strength (nominally 0.1 to 1 millimolar) and preferably containing a relatively low specific conauctivity salt or Dulter. Mixing of the two fluids reduces the conductivity of the fluid in the active element, increases the zeta potential, and decreases Joule heating. There is no absolute limit to die strength of the ionic fluid that may be used. A system can be designed so that a fluid of any ionic strength fluid can be sufficiently diluted to support electrokinetic flow. However, the maximum flow rate for the working fluid will decrease in proportion to its ionic strength.
(h) The ability to use pure solvent working fluids. Some ionic content is required to achieve reasonable electroosmotic performance. Pure solvents are thus poor electroosmotic fluids, particularly in small-pore size media due to problems with charge layer overlap. In such cases the second fluid is preferably selected to be of moderate ionic strength (10 to 100 mM, for example). Mixing of the two fluids provides the ionic content needed for high performance electrokinetics.
(i) The ability to use pure organic working fluids. In many cases pure organic solvents, even with suitable ionic content, provide noticeably lower electrokinetic performance than the same solvents containing even a few percent water. In such cases, the second fluid preferably is aqueous and has a moderate ionic strength. Mixing of the two fluids provides the water content needed for high performance electrokinetics.

Figure 13:
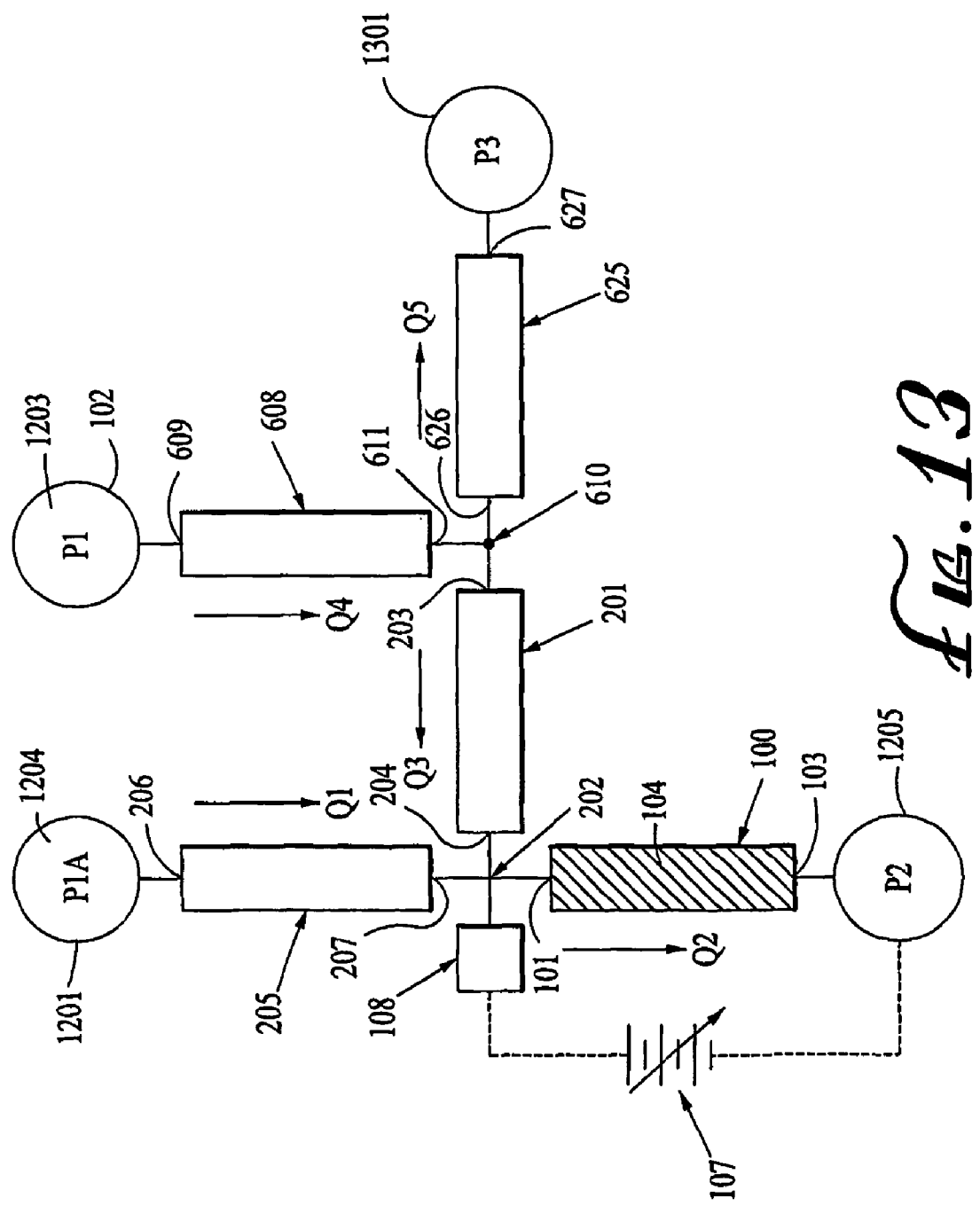
FIG. 13 illustrates a shunt-mode embodiment of the current invention wherein a second fluid is mixed with a working fluid to improve the performance and operating range of the electroosmotically-driven flow controller element.

Another alternative embodiment configured in a shunt-mode is shown in FIG. 13. The first, second and third elements 205, 100, and 201 respectively of FIG. 13 play the same roles as the first, second and third elements 205, 100, and 201, respectively, of FIG. 12. The working fluid 1203 is supplied at pressure $P_1$ to the inlet 609 of the fourth flow element 608. The outlet 611 of the fourth flow element 608 is connected at a second junction 610 with the inlet 203 of the third flow element 201 and the inlet 626 of a fifth flow element 625. A second fluid 1204 is supplied at pressure $P_{1A}$ to the inlet 206 of the first flow element 205. The outlet 207 of the first flow element 205 is connected at a first junction 202 with second and third flow elements 100 and 201, respectively. The second flow element 100 is electrokinetically active and terminates in a reservoir 1205 at pressure $P_2$ that is less than $P_{1A}$ and $P_1$. The second fluid 1204 mixes with the working fluid 1203 at junction 202 to yield a mixture providing acceptable electroosmotic performance of the controller. The fifth flow element 625 terminates at a terminus 1301, for example a chromatograph, at a pressure $P_3$ that is less than $P_{1A}$ and $P_1$. The objective is to control the flow of working fluid 1203 through the fifth element 625.

The pressures at the first and second junctions 202 and 610, respectively, P' and P'' respectively, are determined by solution of $$(P_{1A}-P')k_1+(P''-P')k_3=P''k_2$$

$$(P_1-P'')k_4=(P''-P')k_3+(P''-P_3)k_5$$

where these relations, without any loss of generality, are written with respect to a $P_2$ gauge pressure. Several conditions govern or suggest relationships between the various conductances of the flow elements.

For many applications, particularly in chemical analysis, a goal is to avoid contamination of the fluid flowing through the fifth element 625. In such cases, in a preferred design, the flow conductances are selected to direct the flow through the third element 201 from the second junction 610 to the first junction 202. This requires, for all positive values of a, $$k_1k_4+k_2k_4+(k_1k_5+k_2k_5)P_3/P_1>(k_1k_4+k_1k_5)x$$

It is preferable to exceed this inequality by a factor of at least 1.2 and more preferably by 2 to 3 times. Higher values tend to minimize system-to-system performance variation due to component element part-to-part variations.

Additionally, the third element 201 may be used to prevent the second fluid 1204 from contaminating the fluid flowing through the fifth element 625. This is preferably done with as little head loss as possible. Thus the conductance of the third element 201 is preferably much greater than that of the other elements. Preferably $k_3$ is at least 100 times and more preferably about 1000 to 5000 times larger than the conductance of the other elements.

Preferably, the ratio of the flowrates through the first and third elements 205 and 201, respectively are set, thereby setting the ratio of the two fluids in the mixture reaching the second element 100. This ratio then allows fluid properties that affect the electrokinetic performance, such as pH or the amount of dilution, to be computed. For the case where $P_{1A}=P_1$ (this equality is imposed here for illustration and does not limit the general operation or applicability of the invention)

$$\frac{Q_1}{Q_3} = \frac{k_1}{k_3} \frac{k_2(k_3+k_4+k_5)(1+a)+k_3k_5(1-P_3/P_1)}{k_2k_4-k_5k_1+ak_2(k_4+k_5)+k_5(k_1+k_2)P_3/P_1}$$

Optionally, for example, a flow controller may be designed so that there is a maximum pressure available at the inlet 626 to the fifth element 625, a maximum or minimum flowrate through the fifth element and/or a maximum conductance of the fifth element. Given the conductances determined as described above, setting a minimum flowrate through the fifth element provides a maximum value for a.

In a specific example, $P_{1A}=P_1$, the working fluid 1203 is 10 mM aqueous TFA, the second fluid 1204 is aqueous 500 mM imidazole and 3 mM TFA, and the active element, which is the second element 100, is packed with nominal 0.6 micron non-porous silica particles. For positive flow through the third element 201, $k_2k_4>k_1k_5$. Inspection of the equations reveals that the lowest fraction of second fluid 1204 added to the mixture, a condition that will yield the most acidic pH, occurs for an applied potential to the second element 100 that yields a gauge pressure of zero at the first junction 202. In this limit the ratio of flowrates is:

$$\frac{Q_1}{Q_3} = \frac{k_1}{k_3} \frac{k_3+k_4+k_5}{k_4+k_5P_3/P_1}$$

The design choices in this example with $P_3=0$ suggest conductance values, relative to the value of $k_5$, of about 0.19, 0.14, 3000 and 2.7 for $k_1$ through $k_4$ respectively. The entire set can be scaled to meet the flowrate requirements through the fifth element 625. With these values, the condition for positive flow through the third element 201 is well satisfied. The ratio of flowrates through the first and third element 205 and 201, respectively is sufficient to yield pH values at the inlet 101 of the second element 100 that are greater than about 7.2 over the entire operating range, thus providing for high performance electrokinetics with silica. This set of values also provides a maximum of about 70% of the working fluid source pressure at the inlet 626 of the fifth element 625.

In the embodiment illustrated in FIG. 13, the second fluid 1204 and the working fluid 1203 are combined at the first junction 202 and flow directly into the second element 100. This may not provide sufficient residence time to assure reasonably complete mixing of the two fluids 1203 and 1204. Some amount of mixing is preferred to obtain higher electroosmotic performance.

Figure 14:
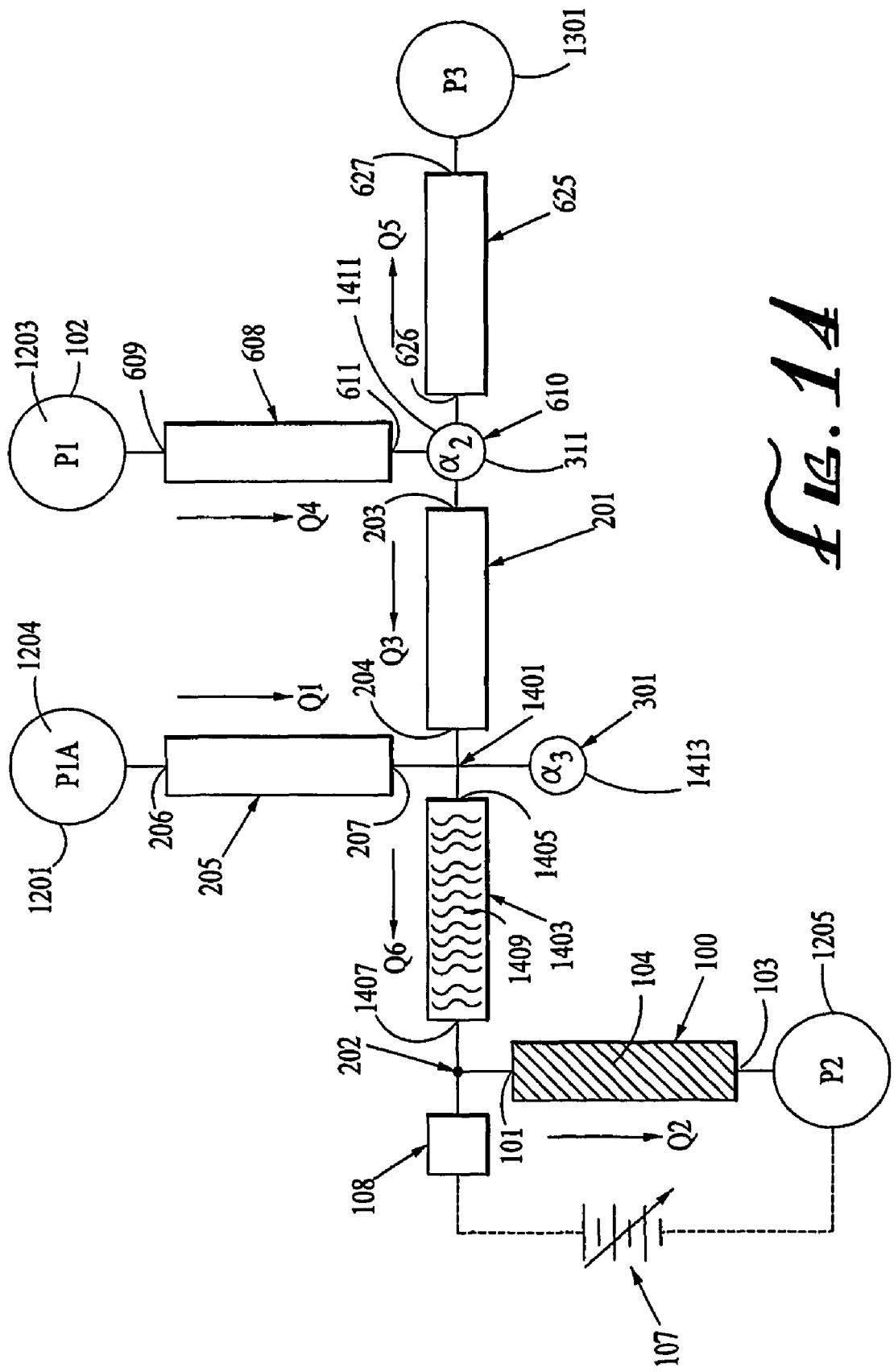
FIG. 14 illustrates an embodiment of the invention that promotes mixing of two fluids before they enter the electroosmotically-driven flow controller element.

In the embodiment illustrated in FIG. 14, the second fluid 1204 and the working fluid 1203 are combined at the third junction 1401. The combined fluids then flow through a sixth element 1403, having an inlet 1405 and an outlet 1407, to the inlet 101 of the second element 100. The finite residence time of the combined fluids in the sixth element 1403 promotes mixing of the two fluids 1203 and 1204.

The flow is in the 'creeping' or 'Stokes' limit. As such, lateral mixing of the two fluids is by diffusion. Thus, the length of the sixth element 1403 preferably is substantially larger, more preferably at least 10 times, and most preferably between 100 and 500 times larger than the quantity $Q_6/2\pi D$, where D is the diffusion coefficient of one fluid into the other. For cases where the sixth element 1403 is not of circular cross sectional shape the 'diameter' is preferably taken as the major diameter of the non-circular shape.

Alternate methods may be employed to promote this mixing. For example, structures that serve to enhance stirring, such as passive or active mixers 1409, as are well known in the art, can be included within the sixth element 1403.

A pair of pressure sensors 301 and 311 are arranged to determine the flowrate through the fifth element 625. These signals can then be employed as part of a servo-loop to control the flowrate by actively adjusting the potential across the active element.

A number of occurrences may introduce an apparent compressibility (fractional change in volume with respect to a change in pressure) into the system and thereby affect the flowrate and flow direction. Such occurrences are not limited to electroosmotic systems and include, but are not limited to: the presence of a bubble of gas; isothermal compression of a fluid; and deflection of the sensor diaphragm.

During a substantial pressure transient, as might occur at first pressurization of the system, the presence of an apparent compressibility, for example, a sensor connected directly at the input of the fifth element 625, may temporarily alter the flow direction through the third element 201 of the embodiment illustrated in FIG. 13. Such a transient flow reversal may temporarily contaminate the second junction 610 with the second fluid 1204.

At initial pressurization, the second fluid 1204 flows through the first element 205 and then some portion may flow through the third element 201 to fill the compressible volume at junction 610. These flows persist until the sensor volume is pressurized, after which the overall flow through the third element 201 is directed from the second junction 610 to the first junction 202 (positive flow).

When $k_3$ is selected to be substantially greater than the conductances of the other flow elements, $a_3/k_1$ is preferably greater than $a_2/k_4$, more preferable at least two times greater than $a_2/k_4$, and most preferably more than 5 to 10 times greater than $a_2/k_4$, in order to have proper flow direction in the third element 201 during the start-up transient. Here, $a=\theta v$, where v is the internal volume of a junction plus any attendant volume or sensor, $\theta$ is the sum of apparent compressibilities within the volume, and $a_2$ and $a_3$ are the a-values associated with the second and third junctions. It will be appreciated that the ratio a/k has dimensions of time and reflects a time-response in the same manner as an RC-time-constant in an electronic circuit.

It is generally preferable to minimize the a-values throughout the system to obtain faster system time response. Thus it is not preferable to satisfy the above condition by making $a_3$ large, rather it is preferable to make $a_2$ small in combination with selecting k4>k$_1$, the latter being wholly consistent with the requirement for positive steady state flow through the third and sixth elements 201 and 1403, respectively.

Alternative methods for assuring positive flow through the third and sixth elements 201 and 1403, respectively during a pressurization transient include but are not limited to:

(a) during system pressurization, initiating pressure P$_1$ before pressure P$_{1A}$ and during system de-pressurization, removing pressure P$_{1A}$ prior to removing pressure P$_1$;

(b) for cases were P$_1$ and P$_{1A}$ are derived from the same source of pressure, a compressible volume, acting as an accumulator that will delay pressurization of the first element, may be added at the 206 inlet to the first element 205;

(c) with the pressure transducer, which acts as a first accumulator 1411, at the second junction, installing a compressible volume, which acts as a second accumulator 1413, at the third junction to provide an appropriate a-value;

(d) with the pressure transducer at the second junction, installing a check valve to direct flow from the second to the third junction.

These methods of assuring positive flow may be used in electroosmotic systems as well as systems having no electroosmotic activity.

The devices shown thus far employ a single active element 100 and rely on prudent selection of conductances to passively control the ratio of the fluids in the mixture reaching the active element. Active control of other component conductances and driving pressures can add flexibility and loosen design constraints. FIG. 15 shows two electrokinetically active elements in series as part of a shunt-mode flow controller.

For the shunt-mode controller with mixing, inspection of the equations reveals that the lowest value of the ratio Q$_1$/Q$_3$ occurs for the lowest value of the pressure at the first junction 202. Consider the shunt-mode controller of FIG. 15 included in a mixing system such as the one shown in FIG. 13. For illustration, but not limiting the invention, the lowest operating pressure at the first junction 202 is taken as zero, the pressure P$_3$ is taken as zero, and P$_{1A}$ is taken equal to P$_1$. The ratio of flowrates, in the limit that k$_3$ is substantially greater than the other k-values, is then Q$_1$/Q$_3$=(1+a$_{1max}$)k$_1$/k$_4$, where a$_{1max}$ is the value of a$_1$ for the first element 205 at the voltage needed to reach zero pressure in the first junction 202. The condition for positive flow through the third element 201 (for the case considered in this illustration) is k$_2$k$_4$>k$_1$k$_5$ and generally dynamic range considerations tend to yield values of k$_2$ less than or about equal to k$_5$. Thus, the need to provide a finite ratio of flowrates requires, in this example, a finite value of k$_1$/k$_4$ whereas the condition for positive flow through the third element 201 requires, in this example, reducing the value of k$_1$/k$_4$. A finite positive value of aimax can be used to enhance the ratio of flowrates and thus make it possible to satisfy these opposing conditions on the relative values of k$_1$ and k$_4$. It is preferred that the value of a$_1$ be less than the value of a$_2$, preferably 5 to 10 time less, otherwise the electroosmotic flow through the first element 205 will overwhelm that through the second element 100 and the system will not be able to control the flow through the fifth element 625.

Figure 15A:
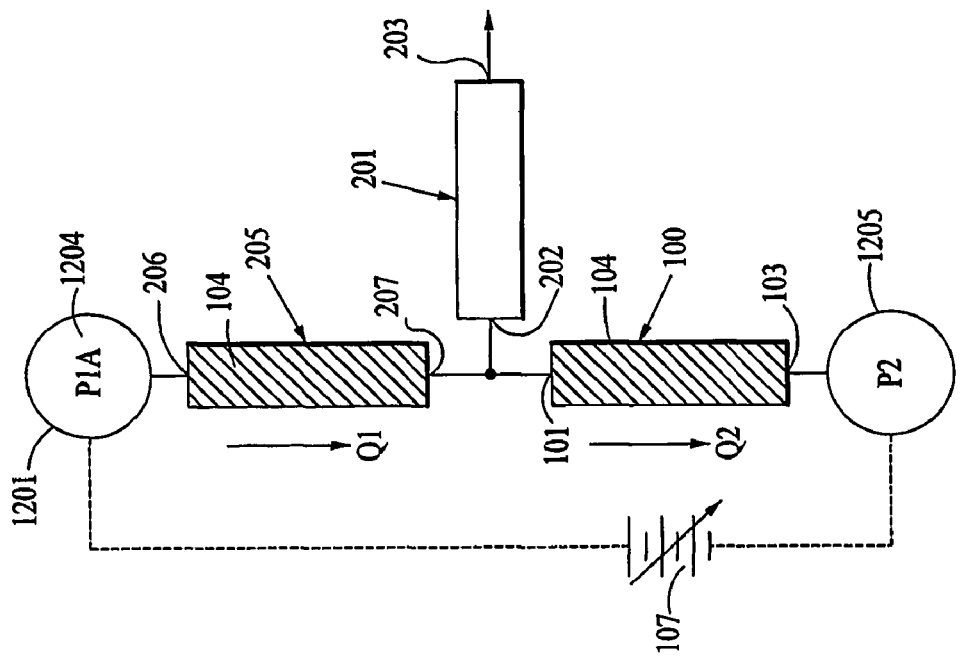
FIG. 15a illustrates an embodiment of the invention having two, separately powered electroosmotically-driven flow controller elements.

In FIG. 15A, the two active elements 100 and 205 have separate power supplies 107 and 1501, respectively, Accordingly the respective electroosmotic flowrates are controlled independently. This control may employ various algorithms possibly enhanced by measuring supply currents or using various sensor inputs.

Figure 15B:
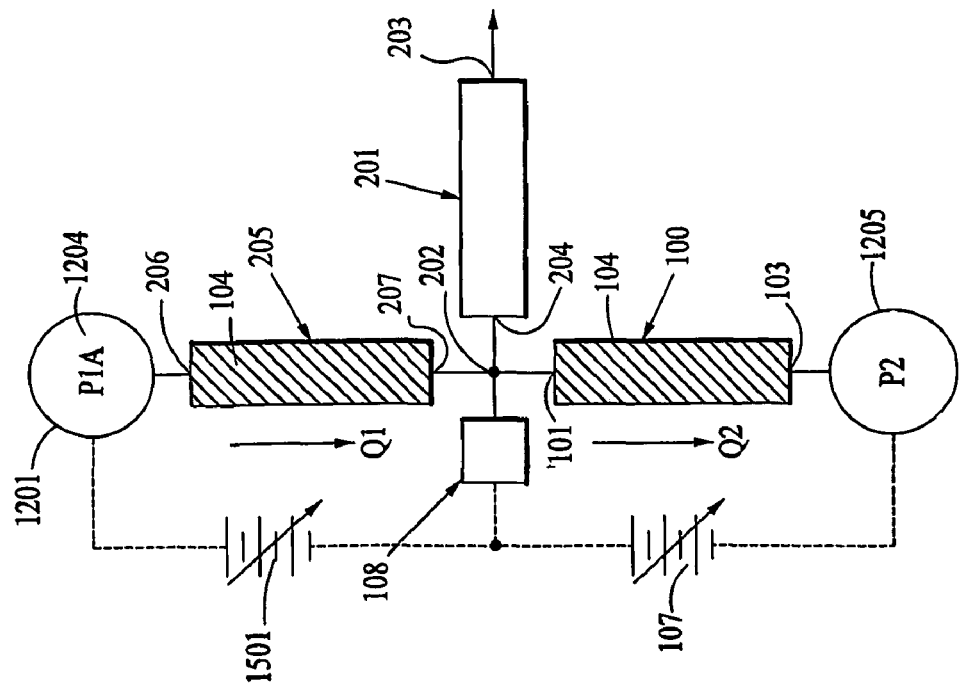
FIG. 15b illustrates an embodiment of the invention having two electroosmotically-driven flow controller elements that share a power source.

In FIG. 15B, a single supply is employed such that a common current is carried through the two active elements 100 and 205, respectively, which are connected electrically in series. In this configuration akP$_1$=sI, where s=v/σ, σ is the electrical conductivity of the fluid as modified by any porous media present, and I is the electrical current. With the common current k$_1$a$_1$/k$_2$a$_2$=s$_1$/s$_2$. The requirement for a$_1$ less than a$_2$ can be satisfied by selection of the material in the first element 205 to yield an appropriate value of the zeta potential with respect to that of the second element 100.

Flow controllers having multiple active elements have been described in light of the fluid mixing configurations revealed. However, such active control schemes are also applicable to and can provide increased range of operation in other flow controller system embodiments that have multiple fluid sources and flow controller system embodiments that have a single fluid.

Figure 16:
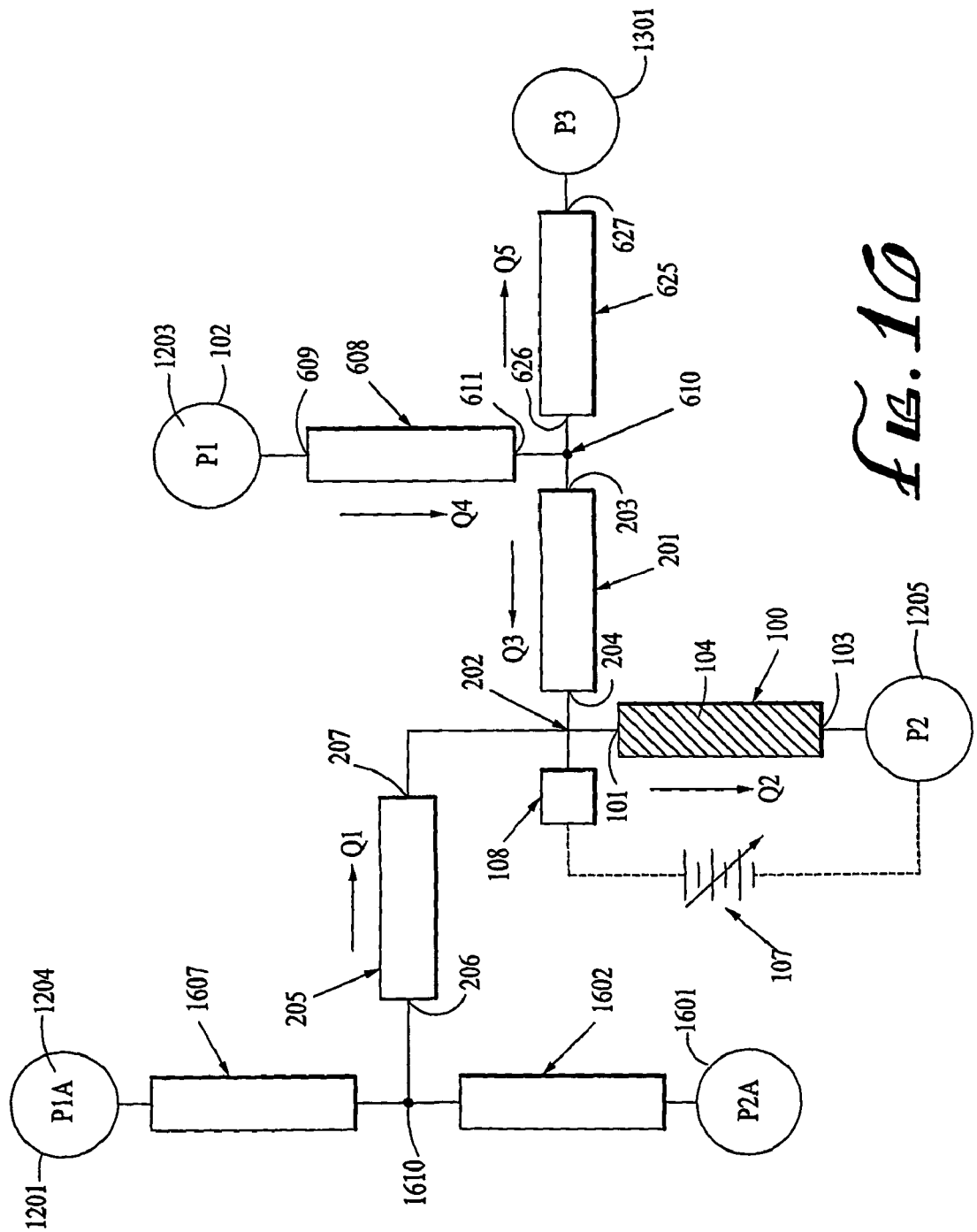
FIG. 16 illustrates an embodiment of the invention in which sixth and seventh flow elements are connected in series between a second fluid source and a drain.

FIG. 16 shows a passive design where sixth and seventh flow elements 1602 and 1607, respectively are connected in series between the source 1201 of the second fluid 1204 supplied at pressure P$_{1A}$ and a drain 1601 at pressure P$_{2A}$ that is less than pressures P$_1$ and P$_{1A}$. The inlet 206 to the first element 205 is connected to the common junction 1610 of sixth and seventh elements 1602 and 1607, respectively. This combination allows the pressure at the inlet 206 of the first element 205 to be reduced from the second fluid source pressure in a fashion much like the use of a resistive voltage divider. This configuration is useful when one wants to use a single pressure source to drive two systems with different pressures.

Alternatively, the sixth element 1602 may be electrokinetically active. This configuration allows the pressure at the junction 1610 to be modulated by varying the potential applied to the sixth element 1602. The two active elements in this embodiment preferably have separate power supplies allowing the respective electroosmotic flowrates to be controlled independently. This embodiment may employ various algorithms possibly enhanced by measuring supply currents or using various sensor inputs.

In the embodiments of flow controllers that are used in conjunction with multiple fluids described thus far, the working fluid is mixed with a second fluid that supports electrokinetic activity. Sometimes, it is desirable that the working fluid not mix with another fluid.

Figure 17:
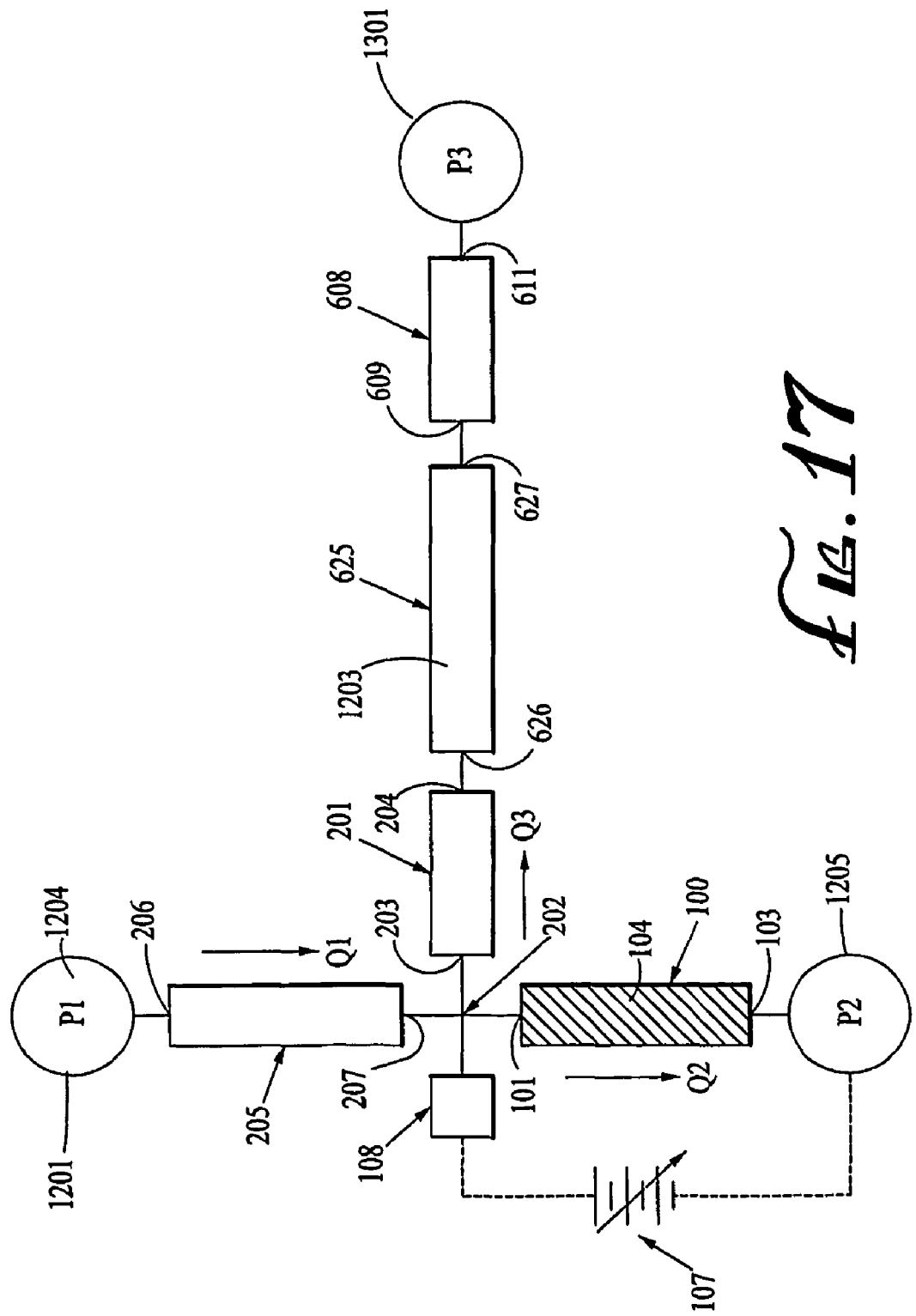
FIG. 17 illustrates an embodiment of the invention that includes a charge of working fluid stored in one of the flow elements.

The embodiment shown in FIG. 17 may be used when this is the case. A charge of working fluid 1203 is stored within the volume of the fifth element 625 also sometimes referred to as a fluid storage element or cartridge. The working fluid 1203 is supplied through the fourth element 608 and then to the terminus 1301 by displacing the working fluid 1203 within the fifth element 625 with the second liquid 1204 supplied through the third element 201. The flowrate of working fluid 1203 is thus controlled by controlling the flowrate of the second liquid 1204 through the third element 201.

The first, second and third elements 205, 100 and 201, respectively form a shunt-mode electroosmotic flow controller. This second liquid 1204 is not necessarily the same as the working fluid 1203 and is selected to support the production of a zeta potential in the second element 100. In this configuration, the number of potential working liquids increases dramatically as the working liquid does not need to be miscible with the second liquid. Nor does the mixture need not support electrokinetic flow. Preferable, however the working liquid is not reactive with the second liquid.

Working liquids include, but are not limited to: all of the working liquids previously listed, oils, hydraulic fluids, gases, slurries (i.e. liquids bearing particulates), emulsions, refrigerants, CFC's, supercritical liquids or mixtures thereof.

The system of FIG. 17 has a time-of-operation limited by the amount of working fluid 1203 stored within the fifth element 625. This time-of-operation may be reduced by any mixing of the two fluids 1203 and 1204 within the fifth element 625. To this end it is preferable that the flow in the fifth element 625 be laminar and that the geometry of the fifth element 625 be selected for a hydraulic diameter that is substantially less than the length of the element, e.g. a length of fine-bore tubing. It is further preferable that the hydraulic diameter be selected to yield a small value of the Peclet number, of the order 0.5 to 20, which is about equal to the product of hydraulic diameter and flow mean velocity divided by twice the diffusion coefficient of one fluid into the other. The use of a fine-bored tube as a liquid storage volume and the use of such a tube inserted in a running stream as a means of dispensing the liquid is well-known and widely used in the arts of liquid chromatography. See, e.g., A. Weston and P. R. Brown, *HPLC and CE: Principles and Practice*, Academic Press, San Diego, Calif., 1997, pp. 83-84. The particulars of evaluating the degree of and controlling mixing in this type of flow and geometry are well known in the arts of mechanical engineering. See, e.g., V. Ananthakrishnan, W. N. Gill and A. J. Barduhn, 'Laminar Dispersion in Capillaries, Part 1. Mathematical Analysis,' AIChE J. Vol. 11 pp. 1063-1072 (1965). G. I. Taylor, 'Dispersion of a solute flowing through a tube,' Proc. Roy. Soc. (London) Vol. 219A, pp. 186-203 (1953). R. Aris, 'On the dispersion of soluble matter in solvent flowing slowly through a tube,' Proc. Roy. Soc. (London) Vol. 235A, pp. 67-77 (1956). P. C. Chatwin and P. J. Sullivan 'The effect of aspect ratio on the longitudinal diffusivity in rectangual channels,' J. Fluid Mech. Vol. 120, pp. 347-358 (1982). M. R. Doshi, P. M. Daiya and W. N. Gill, 'Three dimensional laminar dispersion in open and closed rectangular ducts,' Chem. Eng. Sci. Vol 33, pp. 795-804 (1978).

Figure 18:
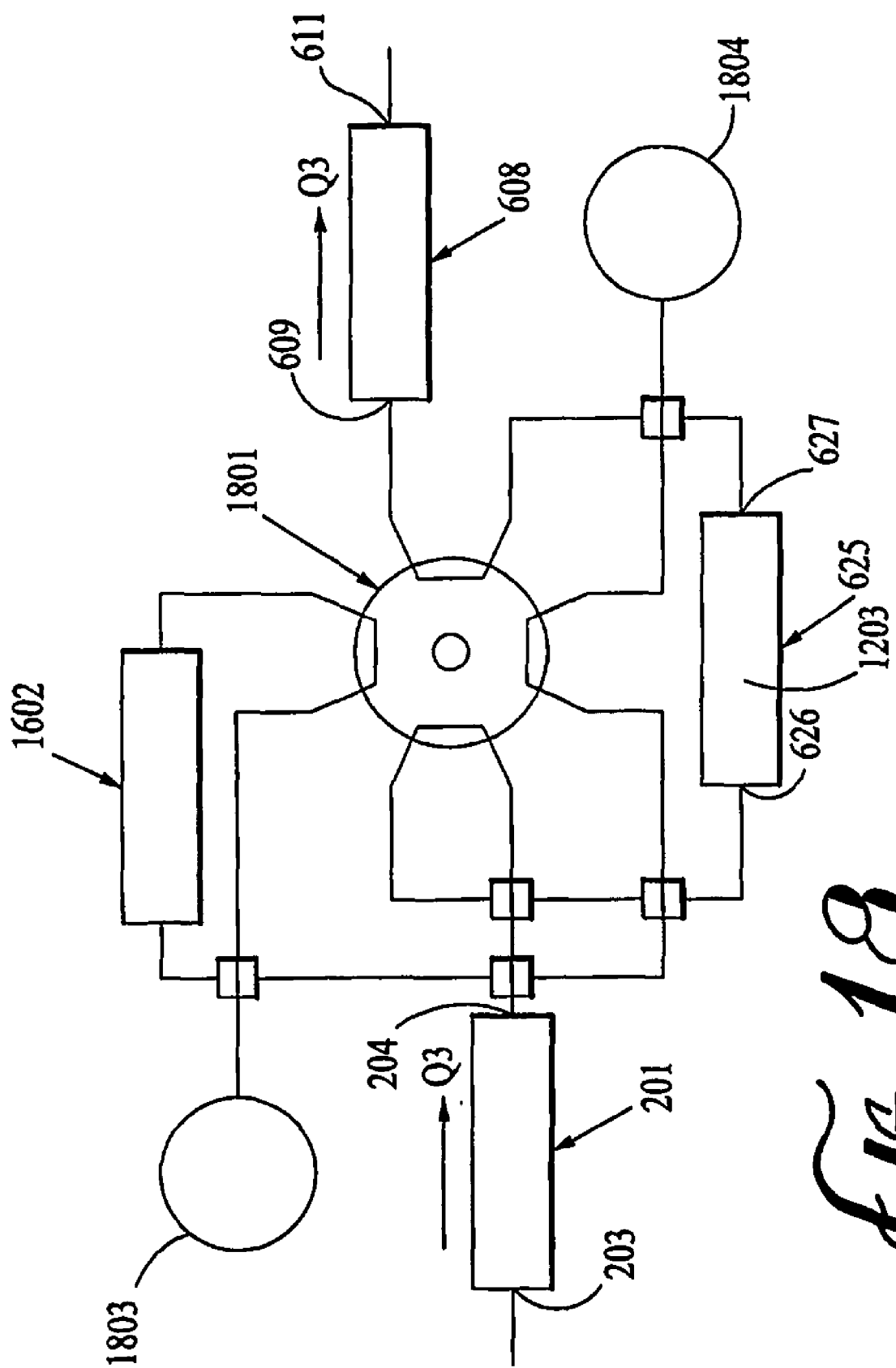
FIG. 18 illustrates a valve configuration that may be used to switch flow elements of flow controllers.

The fifth element 625 of FIG. 17 may be equipped with valving at either end as a means of switching the fifth element in and out of the flow circuit so as to allow flushing of the fifth element and replenishment of the working fluid 1203. FIG. 18 shows a valve 1801 configuration. The valve 1801 may be a rotary valve or a collection of discrete valves or any other configuration known in the arts. The valve 1801 may incorporate one or two or more storage volumes and may be ganged to provide like service to more than one flow controller.

In the embodiment shown in FIG. 18 two working fluid storage volumes 625 and 1602 are in operative association with the valve 1801. These two elements 625 and 1602 need not be identical or have the same internal volume. The working fluids 1203 in these two elements 625 and 1602 need not be the same.

The flow through the third element 201 is routed through the fifth element 625 and then through the fourth element 608. The sixth element 1602 is shown connected between the source 1803 and the drain 1804 of the working fluid 1203. In this configuration, the working fluid 1203 from the fifth element 625 is supplied to the inlet 609 of the fourth element 608 while the sixth element 1602 is flushed and filled with new working fluid 1203. At some selected time the valve 1801 is actuated, ⅛ turn counterclockwise for the device of FIG. 18, to switch the roles of the fifth and sixth elements 625 and 1602, respectively. At some selected later time the process is reversed and so on. This allows continuous delivery of the working fluid 1203 or switching of the working fluids, with some minor disruption during valve actuation.

The flowrate and the volume of the stored liquid determine the maximum time of operation, whereas the size of the volume and the conductances of the connected elements determine the response time of the device. It is thus preferable to minimize the size of the storage volume and provide means to switch-in a newly filled storage volume.

For example, in the system as shown in FIG. 17, equipped with a rotary valve element as shown in FIG. 18, used for delivery of a working fluid for chemical synthesis, the working fluid can be acetonitrile possibly containing some small amount of an organic acid, e.g. formic or acetic acid. A controlled flowrate of working fluid in the range of 100 to 500 nL/min at load pressures in the range of zero to 25 psi above ambient, for example, is desired. The second liquid 1209 can be aqueous 10 millimolar TRIS and about 5 millimolar acetic acid. The source pressure $P_1$ can be between about 500 and 600 psi. The second element 100 can be a 3 cm long, 150 micron inner diameter, "ID," capillary filled with nominal 0.7 micron diameter non-porous silica beads. The first, third and fourth elements 205, 201 and 608, respectively can be simple capillaries. The fifth element 625, and sixth element 1602, if used, can be a length of 0.03 inch ID tubing. The pressure difference across the fourth element 608 can be used to monitor the flowrate.

A design using conductances for the first and fourth elements 205 and 608, of about 1.8 and 5 nl/min·psi, hence lengths of 10 micron ID capillary of about 6.2 and 5.7 cm, provides for a desired range of delivery pressure and flowrate using potentials applied to the second element 100 in the range of about 0.95 and 2.5 kV. The third element 201 can be simply a length of tube or capillary having a substantially larger conductance than the first, second and fourth elements 205, 100, and 608, respectively. The third element 201 can serve several roles: a connector between the first junction 202 and the valve 1801; provide electrical isolation between the bridge connection 108 and the valve 1801; and minimize any back diffusion or mixing of working fluid 1203 into the first junction 202 that might occur during start-up or switching of the valve 1801. The length of the fifth element 625 can be selected to be about 110 cm thereby providing about 16 hours of uninterrupted run-time at the maximum delivery flowrate in this example. The time constant for this embodiment is about 15 seconds. In this design, the roles of the third and fourth elements 201 and 608, respectively, may be reversed.

Figure 19:
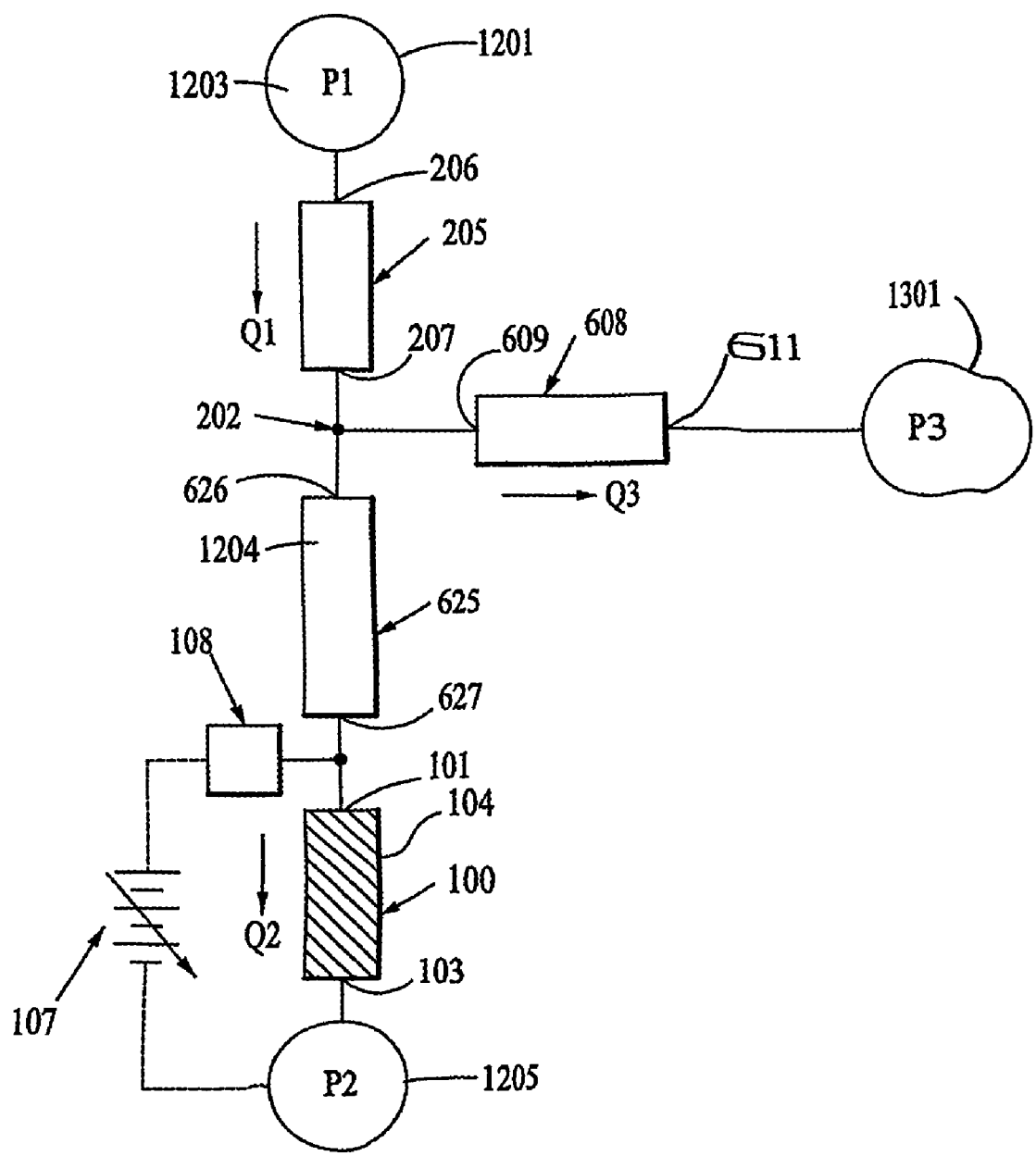
FIG. 19 illustrates an embodiment of the invention that includes a charge of a fluid stored in one of the now elements, wherein the fluid is selected w support electroosmotic function of the electroosmotically active element.

In an alternative embodiment, the storage element may be placed before the active flow controller element. Such a configuration is shown in FIG. 19. The working fluid 1203 is supplied at pressure $P_1$ and passes through the first and fourth elements 205 and 608, respectively. The fluid storage element 625 is placed before the electroosmotically active second element 100 and filled with a second fluid 1204 that is designed to support the electroosmotic function of the second element. As the device is operated, the working fluid 1203 displaces the second fluid 1204 stored in the fifth element 625. This embodiment is subject to the same time response and time-of-operation limitations as the previously discussed embodiment. It may also be used with switchable valves and multiple storage elements. One benefit of this embodiment is that the second fluid 1204 is never present in the working fluid 1203 delivery stream and therefore cannot contaminate the output fluid. Instead, the potential for accidental contamination is transferred to the second element 100, which may be more acceptable in certain applications.

Figure 20:
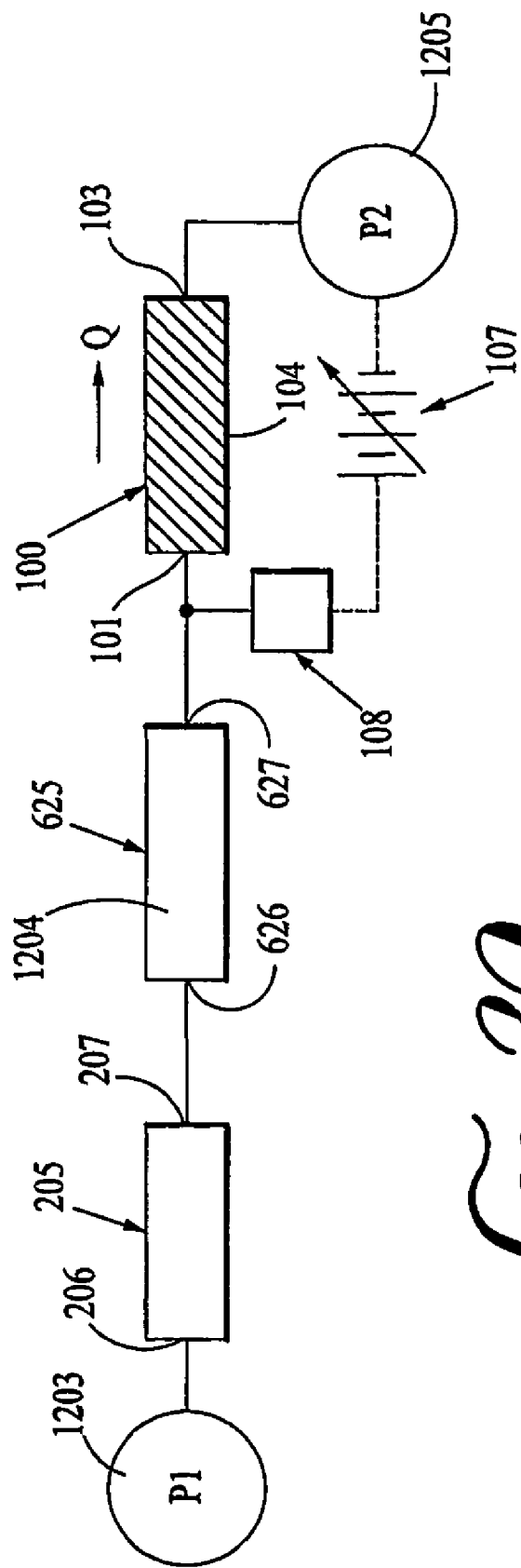
FIG. 20 illustrates a series-mode embodiment of the invention that includes a charge of a fluid stored in one of the flow elements, wherein the fluid is selected to support electroosmotic function of the electroosmotically active element.

Placing a storage element before the electroosmotically active element is also easily realized in a series-mode controller format, as depicted in FIG. 20. The fifth element 625 serves as the storage element for fluid 1204 that supports the electroosmotically active second element 100.

The invention claimed is:

1. An apparatus suitable for use in causing a working fluid to flow from a first point to a second point through a channel by applying a driving pressure to the working fluid at the first point, wherein (a) at least part of the driving pressure is provided by a driving fluid different from the working fluid, (b) the rate of flow of the driving fluid comprises a hydrostatic component and an electroosmotic component, and (c) the driving fluid does not mix with any working fluid reaching the second point, comprising:
  (1) a channel which includes an inlet and an outlet, and through which a fluid under pressure can flow from the inlet to the outlet;
  (2) a porous solid dielectric material which is positioned within the channel between the inlet and the outlet; and
  (3) electrodes which are positioned so that, when an electrokinetic fluid under pressure is flowing through the channel between the inlet and the outlet, the rate at which the fluid flows can be changed by changing an electric potential connected to the electrodes;

said apparatus having at least one of the following characteristics:
  (a) it comprises a flow control element through which a fluid under pressure can flow before reaching the inlet;
  (b) it comprises a flow control element through which a fluid under pressure can flow after leaving the outlet;
  (c) it comprises an operable device which:
    (i) employs a pressurized fluid in its operation; and
    (ii) is connected to:
      (a) the outlet, so that when pressurized fluid flows from the outlet, it passes through the device, or
      (b) a first outlet of a conduit having a second outlet connected to the channel and an inlet which can be connected to a source of pressurized fluid;
  (d) it comprises a first source for a first fluid and a second source for a second fluid, both the first source and the second source being connected to the inlet so that pressurized fluid from the sources can pass through the inlet into the channel;
  (e) it comprises a variable power supply connected to the electrodes;
  (f) it comprises at least one sensor for monitoring a control signal, and a feedback control mechanism operatively connected to the sensor, whereby, when the apparatus includes a power supply connected to the electrodes, the feedback control mechanism modulates the electric potential supplied by the power supply;
  (g) it comprises a conduit having (i) a first conduit outlet which is connected to the inlet, (ii) a second conduit outlet which can be connected to an operable device or a plurality of operable devices, and (iii) a conduit inlet which can be connected to a source of pressurized fluid, whereby, when pressurized fluid enters the conduit, a part of the pressurized fluid flows through the channel and the remainder of pressurized fluid flows through the device or devices;
  (h) it comprises two or more said channels and a conduit having (i) a plurality of conduit inlets connected to an inlet or an outlet of each of said channels, and (ii) a conduit outlet which can be connected to an operable device or a plurality of operable devices; and
  (i) it comprises two or more said channels, the dielectric materials in the channels being different from each other.

2. The apparatus according to claim 1, wherein the porous dielectric material comprises a fused silica capillary, silica particles, an organic polymer, or a product made by lithographic patterning, lithographic etching, direct injection molding, sol-gel processing, or electroforming.

3. The apparatus according to claim 1, comprising a power supply connected to the electrodes, the power supply having one or both of the following characteristics:
  (i) it is a variable power supply, and
  (ii) it is connected to the electrodes through a bridge.

4. The apparatus according to claim 1, comprising at least one sensor for monitoring a control signal, and a feedback control mechanism operatively connected to the sensor, whereby, when the apparatus includes a power supply connected to the electrodes, the feedback control mechanism maintains the control signal within a predetermined range by modulating the electric potential supplied by the power supply, the sensor being one or more of a pressure transducer, a flowmeter, a temperature sensor, a heat flux sensor, a displacement sensor, a load cell, a strain gauge, a conductivity sensor, a selective ion sensor, a pH sensor, a flow spectrophotometer, and a turbidity sensor.

5. The apparatus of claim 1, wherein the driving fluid has a characteristic selected from the group consisting of:
  (a) it comprises a liquid having an ionic strength of least 25 millimolar;
  (b) it comprises a liquid having an ionic strength less than 0.5 millimolar;
  (c) it comprises a liquid having a dynamic viscosity greater than 5 centipoise;
  (d) it comprises a substantially pure organic liquid;
  (e) it comprises a liquid having a dielectric constant less than 20;
  (f) it comprises a liquid containing polyvalent ions;
  (g) it comprises a liquid having a pH value less than 7; and
  (h) it comprises a liquid having a pH value less than 4.

6. The apparatus of claim 1, wherein the sensor is selected from the group consisting of a pressure transducer, a flowmeter, a temperature sensor, a heat flux sensor, a displacement sensor, a load cell, a strain gauge, a conductivity sensor, a selective ion sensor, a pH sensor, a flow spectrophotometer, and a turbidity sensor.

7. The apparatus of claim 1, wherein the driving fluid has a characteristic selected from the group consisting of:
  (a) it comprises a liquid having an ionic strength of least 25 millimolar;
  (b) it comprises a liquid having an ionic strength less than 0.5 millimolar;
  (c) it comprises a liquid having a dynamic viscosity greater than 5 centipoise;
  (d) it comprises a substantially pure organic liquid;
  (e) it comprises a liquid having a dielectric constant less than 20;
  (f) it comprises a liquid containing polyvalent ions;
  (g) it comprises a liquid having a pH value less than 7; and
  (h) it comprises a liquid having a pH value less than 4.

8. An apparatus suitable for use in a method of causing a working fluid to flow from a first point to a second point through a channel, which comprises applying a driving pressure to the working fluid at the first point, wherein (a) at least part of the driving pressure is provided by a driving fluid; and (b) the rate of flow of the driving fluid comprises (i) a hydrostatic component, and (ii) an electroosmotic component, the apparatus comprising:
  (a) a first channel through which a working fluid under pressure can flow;
  (b) a second channel through which a driving fluid under pressure can flow;
  (c) a third channel which includes an outlet and an inlet, the inlet for receiving working fluid from the first channel and for receiving the driving fluid from the second channel, wherein a mixture of the working fluid and driving fluid under pressure can flow from the inlet to the outlet;
(d) a porous solid dielectric material positioned within the third channel between the inlet and the outlet; and
(e) electrodes which are positioned so that, when the mixture is flowing through the channel between the inlet and the outlet, the rate at which the mixture flows can be changed by changing an electric potential connected to the electrodes.

* * * * *